US009889021B2

(12) United States Patent
Park

(10) Patent No.: US 9,889,021 B2
(45) Date of Patent: Feb. 13, 2018

(54) METHOD FOR HIP RESECTION ALIGNMENT APPROXIMATION IN HIP REPLACEMENT PROCEDURES

(71) Applicant: Somersault Orthopedics Inc., Pleasanton, CA (US)

(72) Inventor: Ilwhan Park, Walnut Creek, CA (US)

(*) Notice: Subject to any disclaimer, the term of this patent is extended or adjusted under 35 U.S.C. 154(b) by 0 days.

(21) Appl. No.: 14/582,561

(22) Filed: Dec. 24, 2014

(65) Prior Publication Data

US 2015/0245922 A1 Sep. 3, 2015

Related U.S. Application Data

(63) Continuation-in-part of application No. 14/516,298, filed on Oct. 16, 2014, now abandoned.

(60) Provisional application No. 61/964,209, filed on Dec. 26, 2013.

(51) Int. Cl.
| | |
|---|---|
| *A61F 2/46* | (2006.01) |
| *A61B 17/17* | (2006.01) |
| *A61B 5/055* | (2006.01) |
| *A61B 5/11* | (2006.01) |
| *G06T 7/12* | (2017.01) |
| *A61B 5/00* | (2006.01) |

(52) U.S. Cl.
CPC .......... *A61F 2/4609* (2013.01); *A61B 5/055* (2013.01); *A61B 5/1121* (2013.01); *A61B 17/1703* (2013.01); *A61B 17/1746* (2013.01); *G06T 7/12* (2017.01); *A61B 5/4571* (2013.01); *A61B 5/4585* (2013.01); *G06T 2207/10088* (2013.01); *G06T 2207/20101* (2013.01); *G06T 2207/20168* (2013.01); *G06T 2207/30008* (2013.01)

(58) Field of Classification Search
CPC combination set(s) only.
See application file for complete search history.

(56) References Cited

U.S. PATENT DOCUMENTS

| | | | |
|---|---|---|---|
| 6,928,742 B2 * | 8/2005 | Broers | A61B 5/103 33/227 |
| 2008/0056552 A1 * | 3/2008 | Muller | A61B 5/1075 382/132 |
| 2010/0042105 A1 * | 2/2010 | Park | A61B 17/15 606/87 |
| 2011/0214279 A1 * | 9/2011 | Park | G06T 7/0012 29/592 |

(Continued)

*Primary Examiner* — Tsung-Yin Tsai
(74) *Attorney, Agent, or Firm* — Stephen E. Zweig

(57) ABSTRACT

Aspects of the present disclosure involve systems, methods, computer program products, manufacturing processes and the like, for utilizing a series of images of a patient's anatomy to determine an estimation of relevant lengths and angles and other dimensions for use during a hip replacement procedure, which may be used to create one or more femur and/or acetabulum cavity implants or inserts useful in a partial or total hip replacement. In one particular embodiment, a jig mechanism for providing a scraper of the acetabulum cavity may be created with the information of the patient's anatomy. Further, the location of these features in the images may be determined by analyzing the gray scale value of one or more pixels around a selected point on the image. The pixel with the lowest gray scale value may then be assumed to be the edge of the cortical bone in the 2D image.

19 Claims, 16 Drawing Sheets

(56) References Cited

U.S. PATENT DOCUMENTS

| | | | |
|---|---|---|---|
| 2012/0041446 A1* | 2/2012 | Wong | A61B 17/1703 606/96 |
| 2015/0105698 A1* | 4/2015 | Park | A61B 5/055 600/587 |
| 2015/0125060 A1* | 5/2015 | Park | G06T 7/0012 382/131 |
| 2015/0148807 A1* | 5/2015 | Park | A61B 17/1703 606/89 |
| 2016/0038245 A1* | 2/2016 | Park | A61B 17/155 700/97 |

* cited by examiner

METHOD FOR HIP RESECTION ALIGNMENT APPROXIMATION IN HIP REPLACEMENT PROCEDURES

CROSS-REFERENCE TO RELATED APPLICATIONS

This application is a continuation-in-part and claims priority to U.S. patent application Ser. No. 14/516,298 entitled "METHOD FOR KNEE RESECTION ALIGNMENT APPROXIMATION IN KNEE REPLACEMENT PROCEDURES", naming Ilwhan Park as inventor and filed on Oct. 16, 2014, the entirety of which is hereby incorporated by reference herein. This application also claims priority under 35 U.S.C. § 119(e) to U.S. Provisional Application No. 61/964,209 entitled "FURTHER IMPROVEMENTS IN HIP ALIGNMENT AND RESECTIONING", filed on Dec. 26, 2013, the entirety of which is incorporated by reference in its entirety herein.

TECHNICAL FIELD

Aspects of the present disclosure generally relate to systems and methods for an accurate determination of relevant dimensions and alignments (lengths, angles, etc.) associated with a procedure for partial or total replacement of a hip component of a patient. Additional aspects of the present disclosure generally relate to systems and methods for identifying a cortical bone edge in a two-dimensional image of a hip component of a patient.

BACKGROUND

Through over-use, traumatic events and/or debilitating disease, a person's joint may become damaged to the point that the joint is repaired. One type of procedure to address damage to a person's joint is an arthroplasty procedure. Arthroplasty is a medical procedure where a joint of a patient is replaced, remodeled, or realigned. Damage to the joint may result in a reduction or wearing away of cartilage in the joint area, which operates to provide frictional, compressive, shear, and tensile cushioning within the joint. As such, reduction in cartilage in a joint causes pain and decreased mobility of the joint. To combat this joint pain, a patient may undergo the arthroplasty procedure to restore function and use of the damaged joint.

One type of arthroplasty procedure is known as Total Hip Arthroplasty (THA). In general, THA involves replacing the diseased or damaged portion of the hip with metal or plastic components that are shaped to approximate the replaced portion or shaped to allow movement of the joint and relieve the joint pain. Thus, a THA procedure may include replacement of a portion of the proximal end of the femur and/or a portion of the ilium that make up the hip joint. Similar procedures may be performed on other damaged joints, such as a knee, an ankle, a shoulder, an elbow, and the like. General discussion of arthroplasty procedures herein are directed specifically to THA-type procedures, but may be applied to arthroplasty procedures of other types of joints.

In a THA procedure, a damaged portion of the femur is cut off and replaced with a metal or plastic component that is shaped to mirror or approximate the replaced portion. The metal or plastic component may be impacted onto the femur or fixed using a type of surgical cement or other fastening system. Further, a damaged portion of the ilium may also be removed and replaced with a metal or plastic component that is shaped to mirror or approximate the replaced portion. The ilium replacement implant may also be attached to the ilium through impaction onto the bone or fixed using a type of cement. In essence, the portions of the damaged hip joint are replaced with prosthetic hip components. In general, the femur implant and the ilium implant are mated to form a prosthetic joint that approximates the shape and operation of the replaced hip joint.

As mentioned above, a THA procedure often involves the removal and replacement of portions of the femur and/or ilium of the injured knee. During the removal, the portions of the femur and ilium may be cut, drilled, resurfaced, and the like to create a surface on the bones that mates with the respective implants. In one particular example, the proximal end of the femur may be completely removed to create generally flat surfaces to which the implants are mated. Once the mating surfaces for the implants are created on the receiving bones, the implants may then be attached to the bones as described above.

Although the broad outline of the THA procedures is described above, there is much to consider when performing the procedure. For example, patients may undergo a preoperative planning phase including one or more consultations with a doctor a month or more before the THA is performed. In addition, alignment of the implants in the joint with the rest of the patient's anatomy is crucial to the longevity of the implant and the implant's effectiveness in counteracting the pre-THA joint condition. As such, systems and methods have been developed to produce customized arthroplasty cutting jigs that allow a surgeon to quickly and accurately perform the necessary resections of the bones that result in a successful THA procedure. In particular, cutting jigs may be generally customized for the particular patient's joint undergoing the THA procedure to ensure that the implants align with the patient's anatomy post-procedure. Through the use of such customized cutting jigs, the THA procedure is both more accurate (ensuring more longevity to the implants) and quicker (reducing the time required for the surgical procedure, thereby reducing the potential for post-surgery complications).

In general, cutting guides or cutting jigs used in THA procedures may attach to one or more bones of the hip and provide a cut line to the surgeon for use during the THA surgery. In particular, a femur cutting jig may attach to one or more portions of the proximal end of the femur and include a cut guide or line. A surgeon, during the procedure, inserts a saw device into or through the cut line to resect the proximal end of the femur. In this manner, the end of the femur is resected by the surgeon during the THA procedure, thereby creating a smooth mating surface for the implants. As should be appreciated, the location and angle of the cut plane through the respective bone surface indicated by the cutting jig may determine the overall effectiveness of the THA procedure. As such, a cutting jig utilized during the procedure should be designed to provide the proper location and orientation of the cut plane on the bones of the affected joint such that treatment of the region can be performed accurately, safely, and quickly.

Conventional jigs may be complicated to create, suffer from inaccuracies, overly time consuming to generate, overly expensive to generate, and many other concerns. Thus, while such systems may be useful, there are numerous opportunities to advance the art. It is with these and other issues in mind, among others, that various aspects of the present disclosure were developed.

SUMMARY

One implementation of the present disclosure may take the form of a method for determining an orientation of an implant for an arthroplasty procedure on a human hip joint. The method may include the operations of receiving a plurality of two-dimensional (2D) images of a patient's joint subject to the arthroplasty procedure at a computing device, providing a sequence of interior images of a neck of a femur from the plurality of 2D images of the patient's joint, the interior images corresponding to cross-section images of the neck of the femur and spaced apart by a positive distance, and estimating a center coordinate for each of the sequence of interior images of the neck of the femur, the center coordinate corresponding to a coordinate in a global coordinate system of the plurality of 2D images of the patient's joint. Additionally, the method may include calculating a best fit linear segment corresponding to at least two of the center coordinates for the sequence of interior images of the neck of the femur, estimating a center coordinate and a diameter for an acetabulum feature of the patient from at least one of the plurality of 2D images of the patient's joint, providing an acetabulum cavity cup insert comprising a diameter corresponding to the estimated diameter for the acetabulum feature of the patient from at least one of the plurality of 2D images of the patient's joint, and aligning the center of the acetabulum cavity cup insert with the best fit linear segment corresponding to at least two of the center coordinates for the sequence of interior images of the neck of the femur.

Another implementation of the present disclosure may take the form of a system for processing a medical scan of a patient in preparation for an arthroplasty procedure on a human hip joint. The system may include a network interface configured to receive one or more medical images of a patient's anatomy, a processing device in communication with the network interface, and a computer-readable medium in communication with the processing device configured to store information and instructions. When the information and/or instructions are executed by the processing device, the system performs the operations of receiving a plurality of two-dimensional (2D) images of a patient's joint subject to the arthroplasty procedure at a computing device, providing a sequence of interior images of a neck of a femur from the plurality of 2D images of the patient's joint, the interior images corresponding to cross-section images of the neck of the femur and spaced apart by a positive distance, and estimating a center coordinate for each of the sequence of interior images of the neck of the femur, the center coordinate corresponding to a coordinate in a global coordinate system of the plurality of 2D images of the patient's joint. In addition, the operations may include calculating a best fit linear segment corresponding to at least two of the center coordinates for the sequence of interior images of the neck of the femur and estimating a center coordinate and a diameter for an acetabulum feature of the patient from at least one of the plurality of 2D images of the patient's joint. Further, the system may include an acetabulum cavity cup insert comprising a diameter corresponding to the estimated diameter for the acetabulum feature of the patient from at least one of the plurality of 2D images of the patient's joint, a center of the acetabulum cavity cup insert aligned with the best fit linear segment corresponding to at least two of the center coordinates for the sequence of interior images of the neck of the femur Yet another implementation of the present disclosure may take the form of a method for preparing an acetabulum cavity of a human hip joint. The method may include the operations of receiving a plurality of two-dimensional (2D) images of a patient's joint subject to the arthroplasty procedure at a computing device, providing a sequence of interior images of a neck of a femur from the plurality of 2D images of the patient's joint, the interior images corresponding to cross-section images of the neck of the femur and spaced apart by a positive distance, and estimating a center coordinate for each of the sequence of interior images of the neck of the femur, the center coordinate corresponding to a coordinate in a global coordinate system of the plurality of 2D images of the patient's joint. The method may further include calculating a best fit linear segment corresponding to at least two of the center coordinates for the sequence of interior images of the neck of the femur, estimating a center coordinate and a diameter for an acetabulum feature of the patient from at least one of the plurality of 2D images of the patient's joint, and providing a jig mechanism configured to align a cavity scraper in the patient's acetabulum cavity, the cavity scraper configured to remove at least one bony projection from an exposed surface of the acetabulum cavity, the center of the cavity scraper aligned with the best fit linear segment corresponding to at least two of the center coordinates for the sequence of interior images of the neck of the femur.

DETAILED DESCRIPTION

Figure 1:
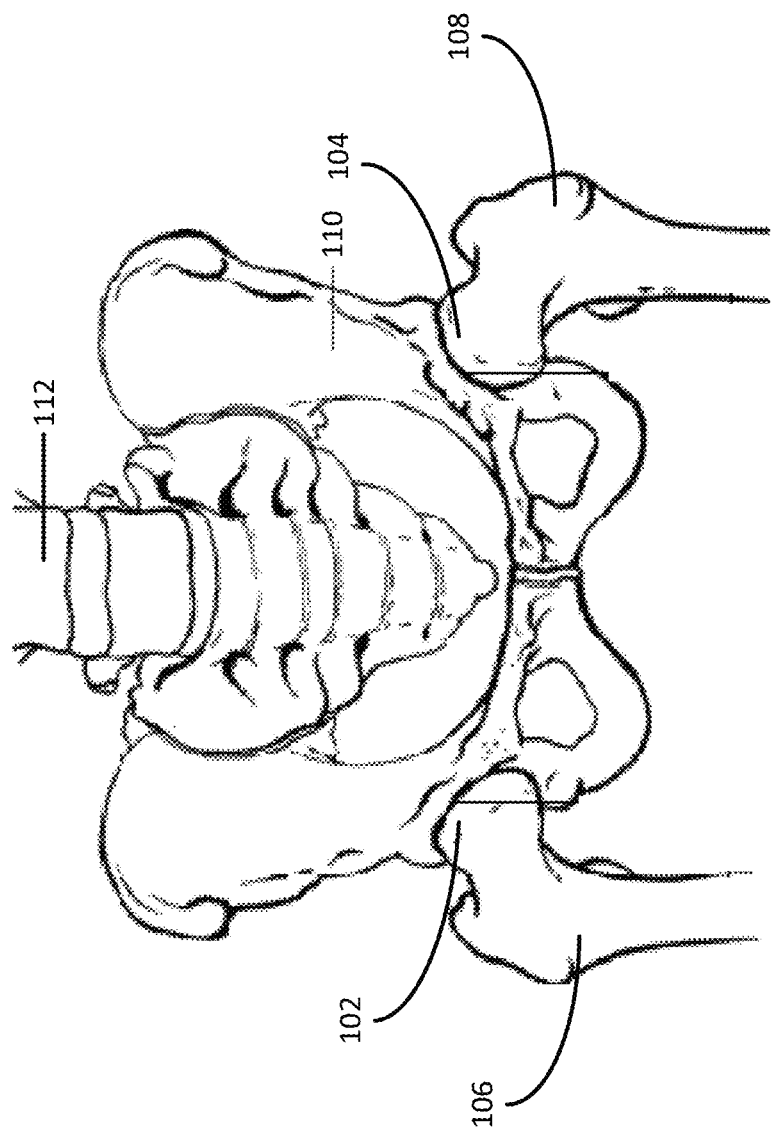
FIG. 1 illustrates an anterior view of a patient's pelvic region.

Aspects of the present disclosure involve systems, methods, computer program products, manufacturing processes and the like, for utilizing a series of images of a patient's anatomy to determine an estimation of relevant lengths and angles and other dimensions for use during a hip replacement procedure, which may be used to create one or more femur and/or acetabulum cavity implants or inserts useful in a partial or total hip replacement. In particular, the present disclosure provides for a method of utilizing one or more two-dimensional (2D) images of the patient's joint to undergo an arthroplasty procedure. The method includes receiving the 2D images of the joint from an imaging device and determining the location within at least one of the 2D images of the patient's cortical bone edge. Ultimately, cutting guides or implants fit to cortical bone (the hard outer bone surface) rather than other parts of the bone being replaced, such as soft tissue surrounding the hip and the like. In general, the location of the cortical bone edge of the patient's hip is determined by analyzing the gray scale value of one or more pixels around a selected point on the image. In particular, a range of pixels around the selected point provides a range of gray scale values that may be analyzed to determine the pixel with the lowest gray scale value. This pixel may then be assumed to be the edge of the cortical bone in the 2D image.

To estimate the relevant lengths and angles for implant placement for use during a hip replacement procedure, the 2D images may be analyzed by a computer program or a user of a computing device to determine several landmarks or aspects of the patient's anatomy. In one particular example, one or more of the landmarks or aspects may be determined through the edge detection of the cortical bone described above. For example, one or more points along a proximal surface of the proximal femur in one or more images of the bones of the hip may be found through the edge detection. With these points identified, the computing device may determine a best fit line through the center of the neck of the femur, as well as a best fit line through the femoral shaft. In addition, an azimuthal angle and a polar angle between the femoral shaft line and the center of the neck of the femur line may also be determined. With these angles determined, a central axis through the acetabulum cavity may be estimated and placement of a femur head implant and acetabulum cavity cup implant may be determined such that the femur head implant resists dislocation from the acetabulum cavity cup implant. As dislocation of the femur implant from the acetabulum cavity implant is often a negative side effect of hip replacement surgeries, proper alignment of the implants based on the patient's anatomy that reduce the likelihood of dislocation may be desired. Further, the procedure to determine the implant positioning does not require the generation of a 3D model of the patient's hip so that the THA procedure may occur more quickly and efficiently than conventional procedures.

To aid in the description below of the customized arthroplasty cutting jigs and methods for creating said jigs, a brief discussion of the bone anatomy of the human hip is now included. As mentioned above, the present disclosure may be applied to any type of joint of a patient. However, for ease of understanding, the discussion herein is limited to particulars of the human hip as an example of the joint relating to the present disclosure procedure and apparatus.

Figure 2:
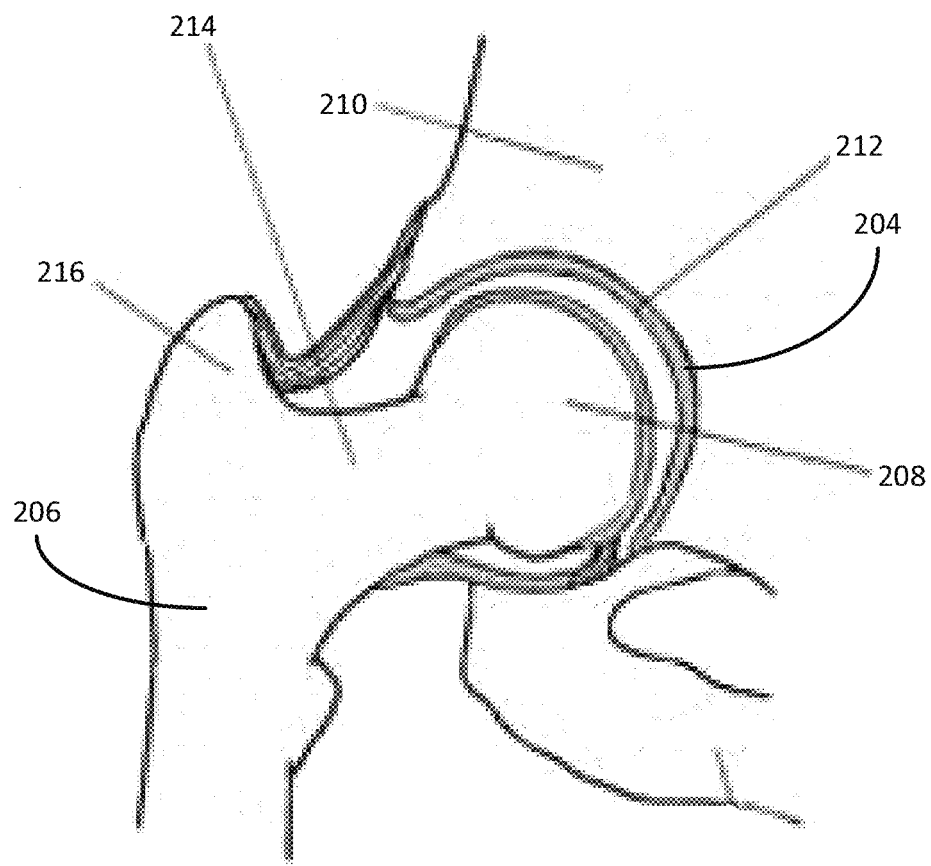
FIG. 2 is a close-up anterior view of a patient's right hip joint.

FIG. 1 illustrates an anterior view of a patient's pelvic region, and in particular, the femur 106-108 and the ilium or acetabulum 110 that comprise the patient's hip joints. In FIG. 1, a right hip joint 102 is shown that includes the patient's right femur 106 and a socket feature in the right side of the patient's acetabulum 110. Similarly, a left hip joint 104 is shown that includes the patient's left femur 108 and a socket feature in the left side of the patient's acetabulum 110. The patient's spine 112 is also illustrated in FIG. 1. A close-up view of the patient's right hip 102 is illustrated in FIG. 2 and discussed in more detail below. However, the features of the right hip joint 102 discussed below are also included in the patient's left hip 104.

As shown in FIG. 2, the patient's right hip joint 202 includes portions of the patient's right femur 206 and a socket feature 204 of the patient's acetabulum 210. More particularly, the hip joint 202 includes the head of the femur 208 resting within the socket 204. Cartilage 212 and other soft tissues may surround the joint 202 to maintain the femoral head 208 within the socket 204. Extending laterally from the generally spherical femoral head 208 is the cylindrically-shaped neck of the femur 214, ending at a large, irregular, quadrilateral eminence of the femur known as the greater trochanter 216. One or more of the components of the hip joint 202 are discussed below with reference to the method for determining implant location for use during a THA procedure.

Figure 3:
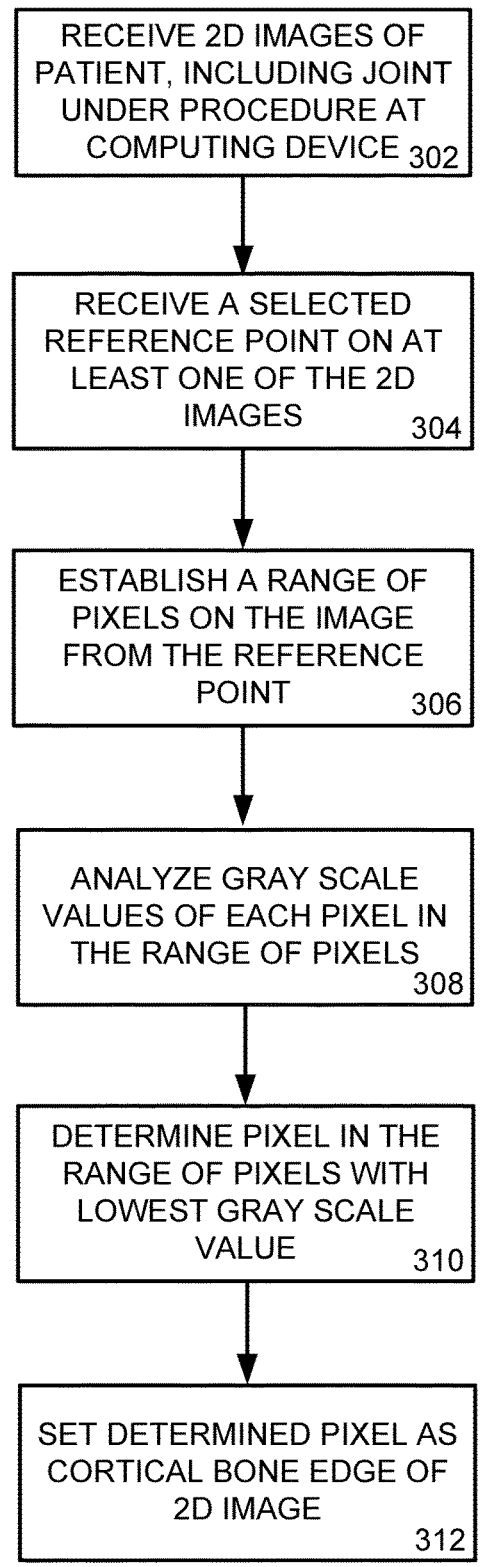
FIG. 3 is a flowchart illustrating a method for locating a cortical bone edge in a two-dimensional (2D) image of a patient's hip.

In general, during a THA procedure, portions of the proximal end of the femur are removed by the surgeon and replaced with respective implants that approximate the shape and function of the end of the bone. Similarly, a corresponding cup insert may be placed within the patient's acetabulum cavity to interact with the femur implant. In partial hip replacement procedures, one or the other implant may be used. To aid in the proper orientation of the implants, the surgeon may employ a cutting jig that provides a cut or resection line for the surgeon to cut along. The cut plane provided by the cutting jig may be determined based on one or more landmarks or features of a patient's anatomy illustrated in an image of the patient's joint. Thus, it may be beneficial for determining the cut plane for the THA procedure to accurately identify the cortical bone, or outer shell, of the patient's femur or acetabulum from one or more image slices of the patient's hip. One method for locating a cortical bone edge in a 2D image of a patient's bone is described in the flowchart of FIG. 3. Although more or fewer operations may be included in the process of detecting the cortical bone of the femur, the operations of FIG. 3 provide an example of one such process that utilizes 2D images of the patient's joint. Further, although described herein in relation to detecting a cortical bone edge of a patient's femur, similar operations may be performed to locate the bone edge of a patient's ilium in the images or any other bone surface of the patient in the images.

Figure 4:
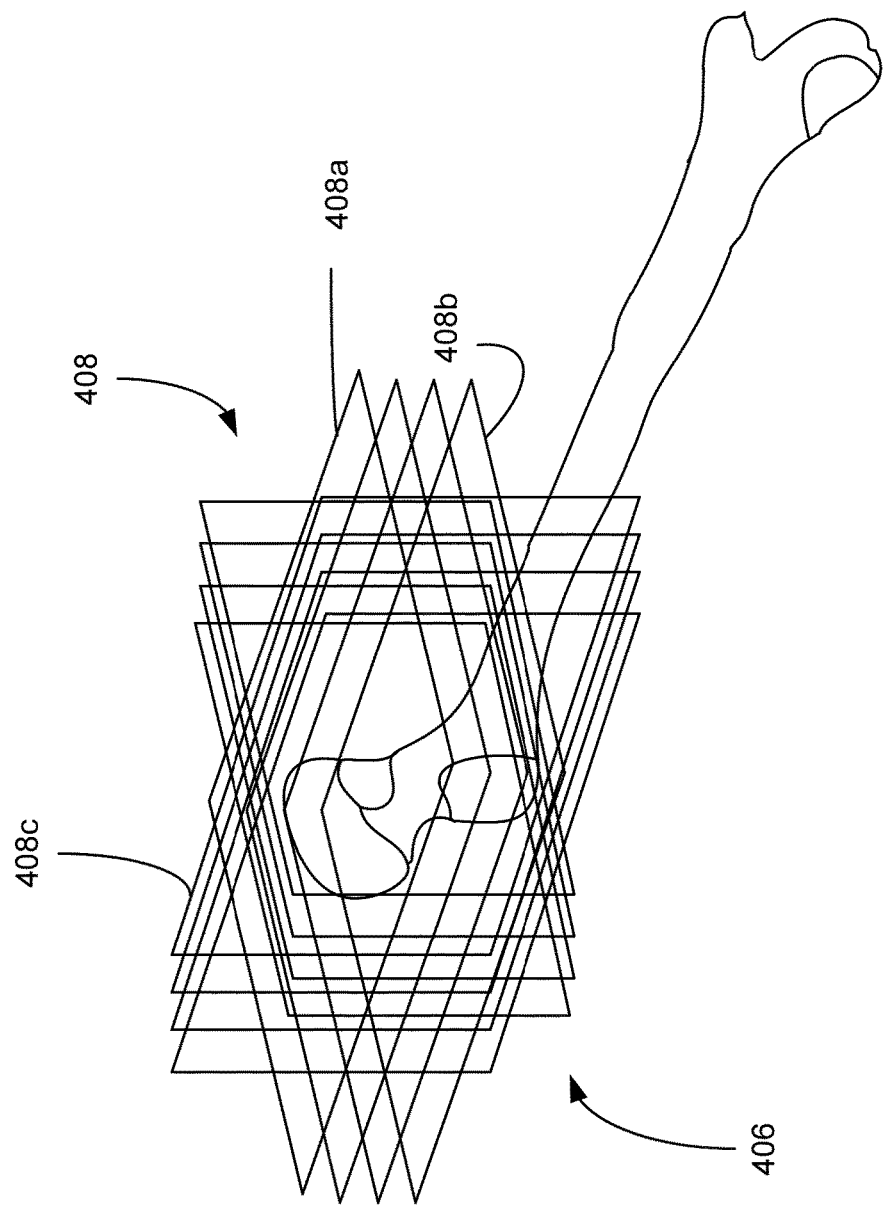
FIG. 4 is an illustration of one embodiment for obtaining 2D images of a hip of a patient.

Beginning in operation 302, a series of two-dimensional (2D) images of the patient's joint on which the arthroplasty procedure is to be performed may be obtained. The 2D images of the patient's joint may be obtained from an imaging device (such as an X-ray or magnetic resonance imaging (MRI) machine) from several aspects of the joint. For example, FIG. 4 illustrates one embodiment for obtaining 2D images of a proximal end of a femur 406 of a patient. In particular, the patient's femur 406 is scanned in a MRI coil to generate a plurality of 2D hip coil MRI images (image slices) of the patient's hip. In one embodiment, the 2D images 408 of the hip include a plurality of image slices taken along a coronal plane 408a through the femur, a plurality of image slices taken along an axial plane 408b through the femur, and/or a plurality of image slices taken along a sagittal plane 408c through the femur. In other embodiments, the 2D images may be any combination of coronal, sagittal and/or axial views. In one embodiment, the MRI imaging spacing for the 2D hip coil images may range from approximately 2 mm to approximately 6 mm and may vary from aspect to aspect. For example, the coronal image slices 408a may be spaced 2 mm apart, while the axial image slices 408b may be spaced 6 mm apart.

While the embodiments herein are discussed in the context of the imaging being via an MRI machine, in other embodiments the imaging is via computed tomography (CT), X-ray, or other medical imaging methods and systems. Further, although it is discussed herein as a scan of the hip, the 2D images may be obtained for any joint or other area of the patient's body, such as images of the patient's ankle, knee, shoulder, etc.

Figure 5:
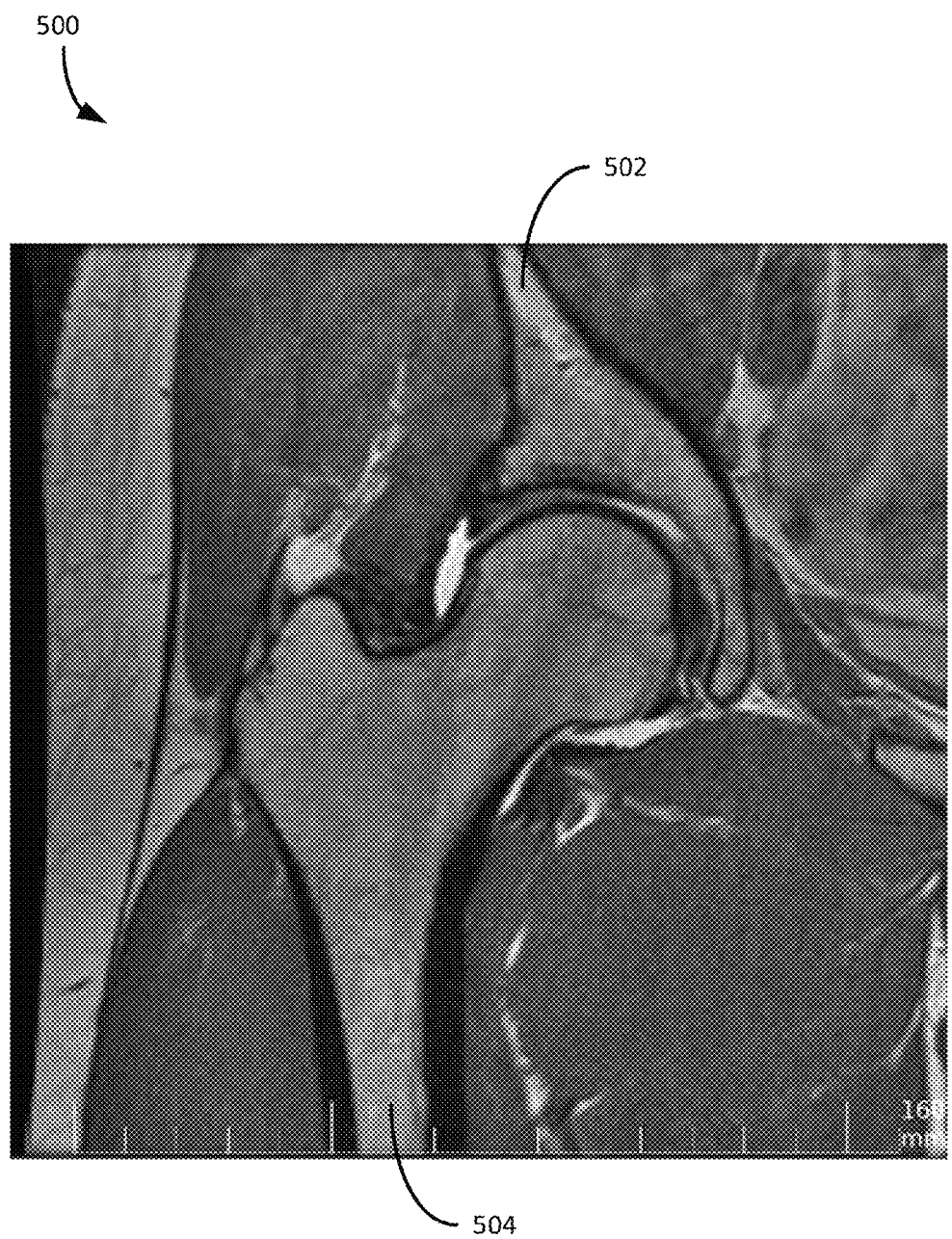
FIG. 5 is a screenshot of a magnetic resonance imaging (MRI) image of a patient's hip.

Once the 2D images of the joint at issue are obtained, the images may be received at or otherwise provided to a computing device for processing. The computing device may receive the images through any form of electronic communication with the imaging device. In one particular example, the 2D images may be obtained by the imaging device (such as the MRI imaging machine) and transmitted to a website (and associated data storage) accessible by the computing device. In general, however, the 2D images may be obtained from the imaging machine in any fashion for further processing by the computing device. One example of such an MRI image of a patient's hip is illustrated in the screenshot of FIG. 5. In particular, the MRI image 500 is a coronal image slice of a patient's hip roughly along a plane through the middle of the hip illustrating the femur ilium 502 and the femur 504 of the hip joint. Although the MRI image 500 of FIG. 5 is referred to for the discussion herein, it should be appreciated that any type of coronal, sagittal, or axial image may be utilized.

In operation 304, the computing device may receive a selected reference point in at least one of the 2D images. To provide the reference point in one embodiment, an operator of the computing device may sit at a monitor or other interface of the computing device through which the images are viewed. Utilizing a software program executed by the computing device, the operator may view the 2D images and provide the one or more reference markers on at least one of the 2D images. These electronic markers may correspond to one or more reference points within the images for use by the computing device to determine a cortical bone portion of the bone illustrated in the 2D image. The operations to utilize the reference points to determine the bone edge or the cortical bone in the image are described in more detail below.

In another embodiment, a program executed by the computing device may obtain the 2D images and determine the one or more reference points within the images, with or without the aid of an operator of the computing device. For example, the computing device may analyze the 2D images and determine a first reference point within the image corresponding to near a presumed cortical bone surface of the bones in the image. In yet another embodiment, one or more of the operations of the method of FIG. 3 are performed by the operator, while other operations are performed by the computer program. For example, a program executed by the computing device may instruct a user of the device to locate a reference point in a particular area of the image by requesting the user to indicate the reference point near what the user may presume to be the cortical bone edge in the image. In another example, the program may analyze the 2D image to locate a potential area in the image that may include the cortical bone of the image and instruct the user to select a reference point within the potential area near a perceived cortical bone feature. As such, any of the operations and methods described herein may be performed by an operator of the computing device or the computing device itself through hardware, software, or a combination of both hardware and software.

Figure 6:
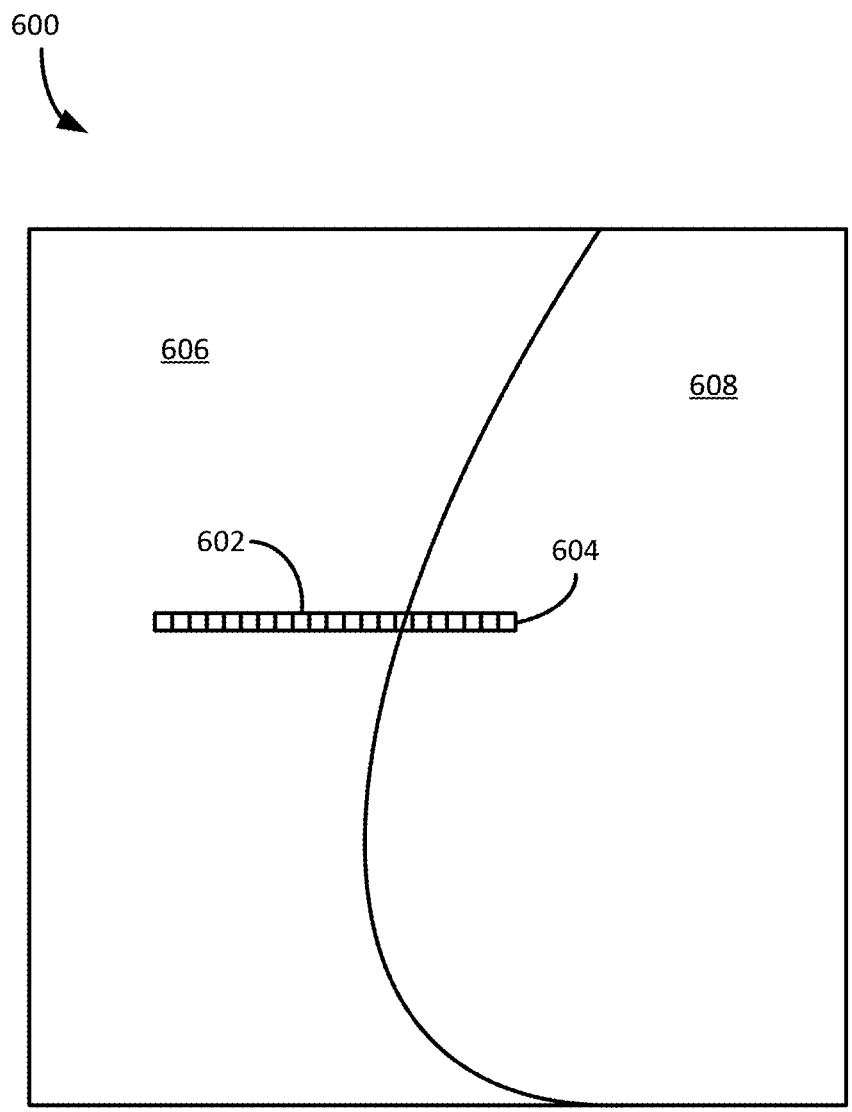
FIG. 6 is a representative screenshot of a close-up view of an MRI image of a patient's femur with a selected point and a horizontal pixel range around the selected point.

FIG. 6 is a screenshot of a close-up view of an MRI image of a patient's femur with a selected point 602 and a horizontal pixel range 604 around the selected point. The image 600 illustrates a non-bone region 606 and a bone region 608 of the patient. For example, the image 600 may represent a small portion of the MRI image 500 shown in FIG. 5 of the patient's hip joint. The image 600 of FIG. 6 illustrates a portion of that image that includes a region 606 illustrating portions of the patient's hip that does not include the image of the femur and a region 608 illustrating portions of the patient's hip that includes the image of femur bone. In one embodiment, the transition from the non-bone region 606 to the bone region 608 indicates the edge of the patient's femur, or the cortical bone of the patient's femur in the image 600.

Also shown in the image 600 of FIG. 6 is the reference point 602. As mentioned above, the reference point 602 may be indicated in the image by the user through operation of the computing device. Thus, the user may analyze the image and select a point on the image at or near the cortical bone of the femur. In another embodiment, the computing device may analyze the image and select a point that is at or near the cortical bone feature of the femur in the image. The reference point 602 may be located in the image 600 in the non-bone region 606 or in the bone region 608. Regardless of the embodiment utilized, it should be appreciated that it is not required that the reference point be at the cortical bone edge in the image 600. Rather, the reference point may be in any position within the image, as discussed in more detail below. However, it may be preferable for the reference point 602 to be located in the image 600 near the cortical bone edge. By placing the reference point 602 near the bone edge in the image 600 ensures that the pixel range 604 captures the bone edge within the pixel range.

Returning to the flowchart of FIG. 3, in operation 306 the computing device may establish a range of pixels 604 in the 2D image around the reference point 602. In the embodiment illustrated in FIG. 6, the range of pixels 604 includes pixels along the same horizontal axis of the reference point 602. In particular, the computing device associates the selected reference point 602 to a particular pixel of the image, referred to herein as the reference pixel. In the embodiment shown, the pixel range 604 is the pixels of the image on either side of the reference pixel 602 in the same horizontal axis of the image as the reference pixel. For example, the pixel range 604 may include the adjacent ten pixels to the left of the reference pixel and the adjacent ten pixels to the right of the reference pixel. That is, the pixel range 602 includes a horizontal row of pixels of the image 600 of twenty-one pixels (the reference pixel, ten pixels to the left of the reference pixel, and ten pixels to the right of the reference pixel). The particular row of the image of the range of pixels 602 is determined from the selected reference point or reference pixel 602 in the image.

As should be appreciated, the embodiment illustrated in the image 600 is but one example of the range of pixels 604 utilized by the computing device. In another embodiment, the range of pixels may be a vertical range of pixels that extend up and down the image from the reference pixel 602. An example of a vertical range of pixels is discussed in more detail below with reference to FIG. 8. In another embodiment, the range of pixels 604 may include a combination of pixels within the same row and same column as the reference pixel 602. In yet another embodiment, the range of pixels 604 may include pixels not in the same row and/or same column as the reference pixel 602, or a combination of pixels in the same row and/or the same column as the reference pixel and pixels not in the same row and/or same column. Further, the range of pixels 604 may not be adjacent to each other within the range such that spaces between the pixels of the range may be present. Also, the range of pixels 604 may include any number of pixels. For example, it is not required that the range of pixels 604 illustrated in FIG. 6 include 21 pixels. Rather, the range 604 may include any number of pixels in the same row of the image as the reference pixel 602. As also discussed in more detail below, the number of pixels in the range of pixels 604 may be selected to increase the likelihood that the cortical bone edge in the image is located within the range. In general, the range of pixels 604 around the selected reference pixel 602 may include any number of pixels in any relation to the reference pixel.

Figure 7:
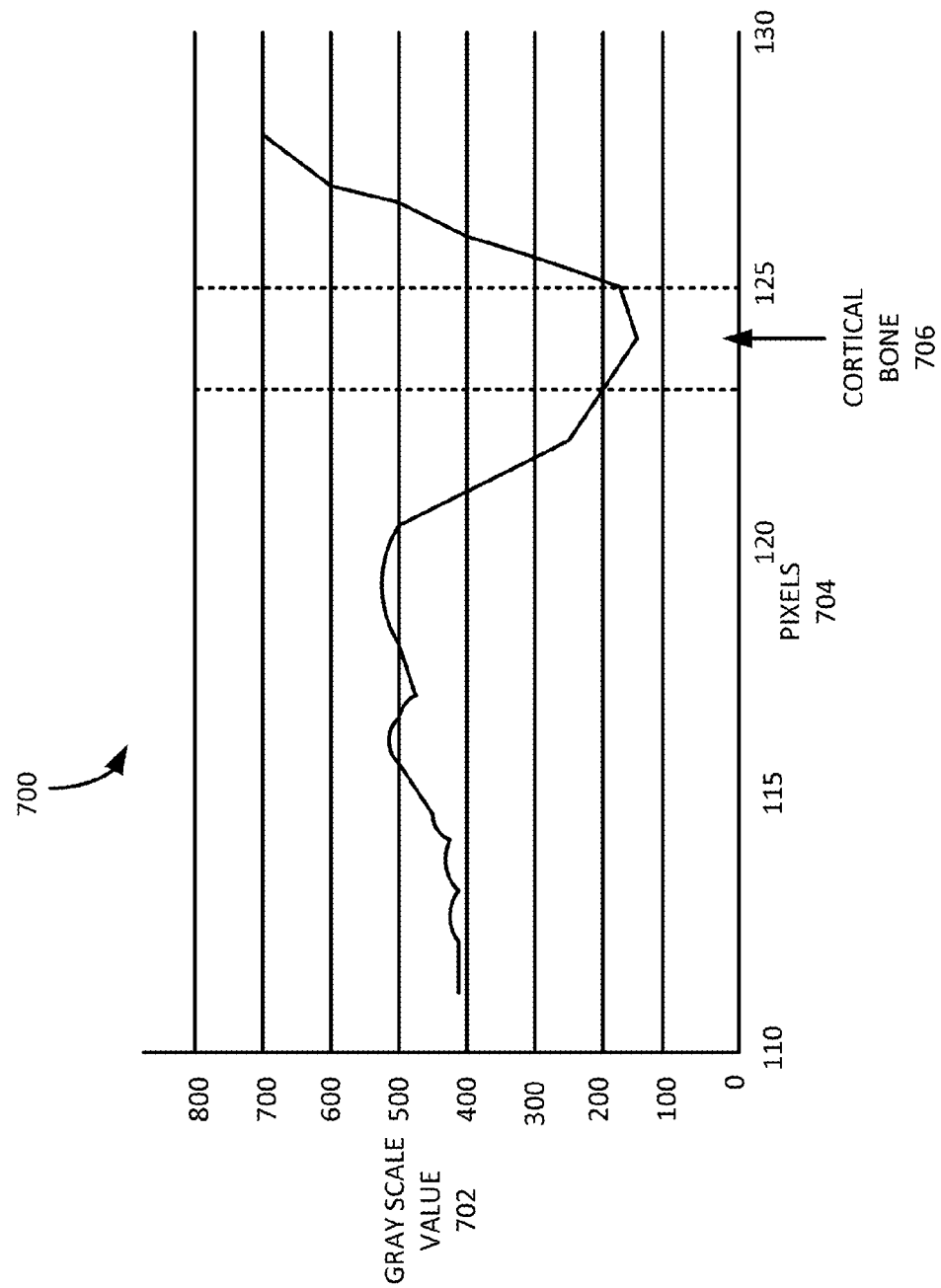
FIG. 7 is a chart illustrating gray scale values of the pixels in the pixel range of the MRI image of FIG. 6.

With the range of pixels 604 for analysis established, the computing device may analyze the gray scale value associated with one or more of the pixels in the range of pixels. FIG. 7 is a chart illustrating the gray scale values of the pixels in the pixel range 604 of the MRI image 600 of FIG. 6. Although shown in FIG. 7 as a chart of the gray scale values of the pixels in the pixel range, it should be appreciated that such a chart may not be created by the computing device. Rather, the computing device may simply analyze the gray scale values associated with one or more of the pixels in the pixel range 604 and determine the lowest value of gray scale in the range. However, for simplification of the discussion herein, reference is made to the chart of FIG. 7.

The chart 700 includes an x-axis of gray scale values of the pixels in the image and a y-axis of a reference number assigned to the pixels in the pixel range 604. In the example shown, the pixels of the pixel range are assigned a reference number from 110 to 130. The reference numbers assigned to the pixels may be associated with the placement of the pixels within the pixel range 604. For example, pixel number 110 may be the leftmost pixel in the pixel range and pixel number 130 may be the rightmost pixel. The reference number provided to each pixel in the pixel range 604 may correspond to a reference number used by the computing device for that particular pixel in the image 600. Thus, pixel number 110 may be the $110^{th}$ pixel in that particular row of the image 600. A similar convention may be used for a vertical pixel range such that the lowest reference number may be assigned to lowest pixel in the vertical pixel range and the highest reference number may be assigned to highest pixel in the vertical pixel range. In general, any type of reference number may be used to index the pixels in the pixel range 604. In one particular example, the pixels in the image are assigned a pixel number by the computing device that is universal to the image and the reference number in the chart may be associated or the same as the pixel number assigned by the computing device.

As shown in the chart 700, the gray scale values 702 for each of the pixels 704 in the pixel range 604 are graphed. In operation 310 of the flowchart of FIG. 3, the computing device may analyze the gray scale values 702 of the pixels 704 in the pixel range to locate the pixel or pixels with the lowest gray scale value. In the graph 700, the lowest gray scale value 706 occurs at or about pixel 124. Once the pixel with the lowest gray scale value is determined by the computing device, the computing device may then associate the location of the pixel with the lowest gray scale value in the range of pixels as the cortical bone edge of the image in operation 312. In general, the transition in the image from a darker region to a lighter region may indicate the cortical bone edge in the image. Thus, the location of the pixel in the pixel range 604 with the lowest gray scale value indicates the cortical bone edge in the accompanying image.

In another embodiment, the computing device may be configured to not only identify the pixel with the lowest gray scale value, but may also verify that the gray scale values along the pixel range provide a valley shape to the graph. The valley shape provides a stronger indication that the cortical bone edge is located at the lowest point within the valley as the gray scale values transition from a dark region to a light region and back to a dark region along the pixel range. Such a valley suggests the cortical bone edge in the image resides in the valley portion of the gray scale value chart 700. In particular, as the x coordinate (704) increases in the graph 700, the gray scale intensity of pixels within the range of pixels tends to decrease to a lowest number, corresponding to a highest bone density, then increase beyond that point. Further, in some embodiments the computing device may indicate more than one pixel in the range as being associated with the cortical bone edge in the image. In this embodiment, a group of pixels may be designated as providing the cortical bone edge such that the computing device may assume the cortical bone edge in the image resides somewhere within the group of pixels. One such group of pixels in which the cortical bone edge lies in shown in chart 700 as pixels 123-125.

As mentioned above, the computing device may analyze the pixels of the range of pixels to determine the pixel with the lowest gray scale value. In one embodiment, the computing device may calculate the lowest gray scale value of the range of pixels where the pixel intensity can be approximately expressed as:

$$I(x,y_m)=p0m+p1mx+p2mx^2+p3mx^3+p4mx^4, (x=n=n0, m0+1,\ldots)$$

where the row index x assumes values x=1, 2, 3, . . . and the coefficients p0*m*, p1*m*, p2*m*, p3*m*, and p4*m* can be found by inversion of a 3×3 or 4×4 matrix involving powers of the pixel index numbers, n=n0, n0+1, n0+2, n0+3, n0+4. The $4^{th}$ degree of polynomial I(x,$y_m$) in the equation may be less than 4 in appropriate circumstances. An approximation for a location of the "center" of the cortical bone can be estimated by a solution x=(x(min;m) (n0≤x(min)≤n0+4) of the equation $$dI(x,y_m)/dx=p1m+2p2mx+3p3mx^2+4p4mx^3=0.$$

Figure 8:
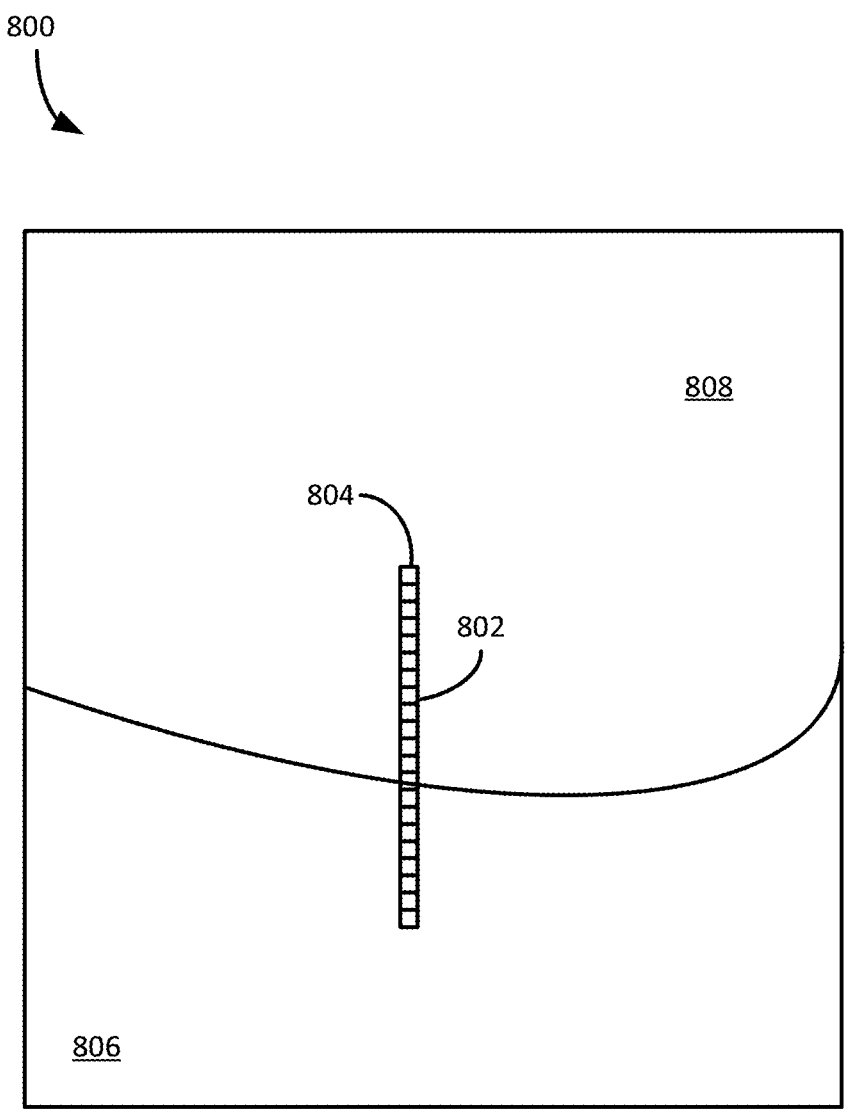
FIG. 8 is a screenshot of the MRI image of the patient's femur with a selected point and a vertical pixel range around the selected point.

The method for determining the cortical bone edge in the image of the patient's femur may also be utilized for other types of pixel ranges. As mentioned above, the pixel range may be a vertical range, or a number of pixels in the same column as the reference pixel. FIG. 8 is a screenshot of the MRI image 800 of the patient's femur with a selected point 802 and a vertical pixel range 804 around the selected point. Similar to the screenshot discussed above with reference to FIG. 6, the image 800 may include a reference point 802 associated with a reference pixel of the image. A range of pixels 804 may also be oriented around the reference pixel. However, in this example, the range of pixels 804 forms a vertical column of pixels around the reference pixel. The orientation of the range of pixels 804 is just one example of the orientation of the range of pixels associated with the reference point.

In one embodiment, the orientation of the range of pixels may be known by the computing device when requesting the location of the reference point from the user of the computing device. For example, the computing device may request the user place the reference point in the image near a particular cortical edge of the bone of the image, such as the outer edge of the medial condyle of the femur in the image. Based on this request, the computing device may then create a horizontally-oriented range of pixels around the selected reference point to capture the cortical bone edge of the femur in the image. Similarly, the computing device may request the user place the reference point in the image near the most distal point of the femur in the image. Based on this request, the computing device may then create a vertically-oriented range of pixels around the selected reference point to capture the cortical bone edge of the femur in the image. In this manner, the computing device may request the placement of the reference point near a particular edge of the femur in the image and apply a range of pixels accordingly. In yet another embodiment, the computing device may analyze the image, select a particular reference point corresponding to a particular edge of the femur, and apply a particular orientation of a range of pixels around the reference point to attempt to capture the cortical bone edge of the femur in the image.

Figure 9:
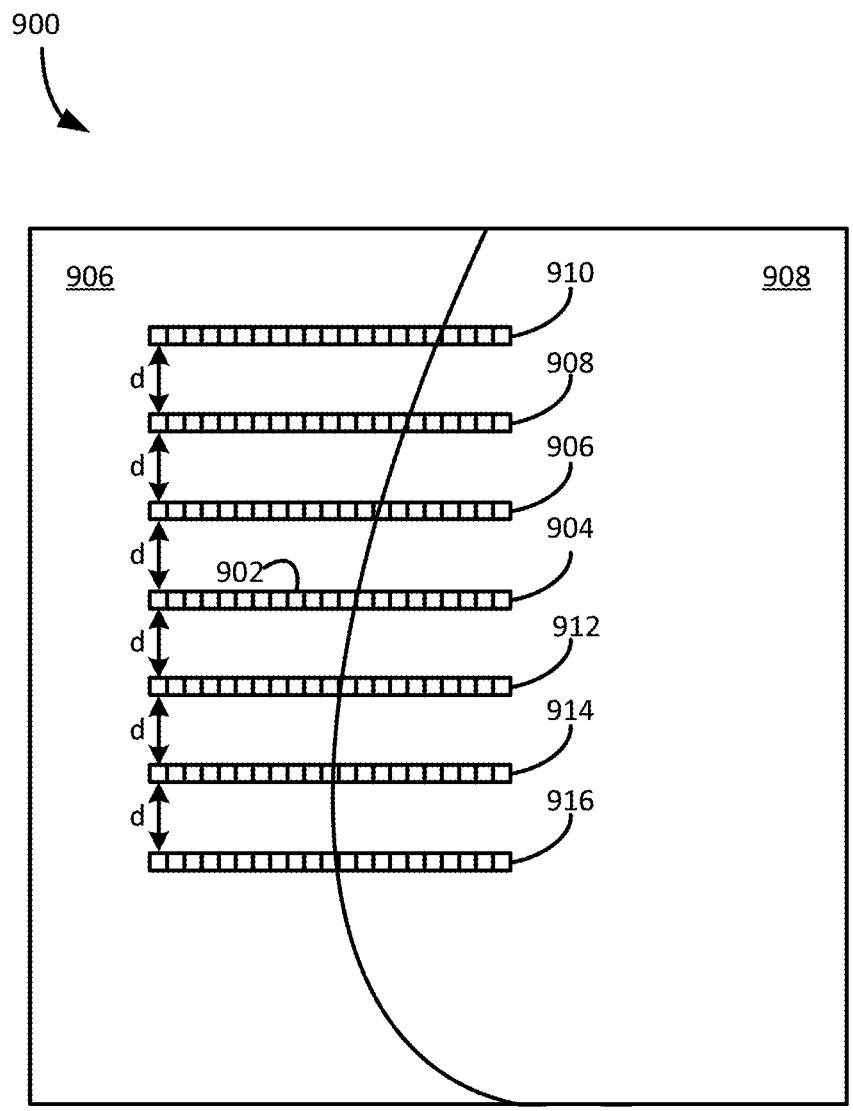
FIG. 9 is a screenshot of the MRI image of the patient's femur with a plurality of horizontal pixel ranges extending from a selected point by a set distance value.

In addition, the computing device may also be configured to analyze several ranges of pixels in relation to determining the edge of the bone in an image based on a reference point in the image. For example, FIG. 9 is a screenshot of the MRI image of the patient's femur with a plurality of horizontal pixel ranges extending from a selected point by a set distance value. The image 900 is similar to the images described above with relation to FIG. 6 and FIG. 8. Also similar to the above description, the computing device may receive a reference point 902 from a user of the computer device or from an analysis of the image 900 by the computing device. A first range of pixels 904 may be created around the reference pixel 902 as described above and analyzed to determine a lowest gray scale value within the range of pixels. However, in addition to locating the pixel with the lowest gray scale value in the first range of pixels, the computing device may create additional ranges of pixels to further locate the cortical bone edge in the image.

In particular, the computing device may be configured to create additional ranges of pixels 906-916 in relation to the first range of pixels 904. For example, a second range of pixels 906 may be oriented a distance "d" from the first range of pixels in any direction. In the particular example illustrated in FIG. 9, the second range of pixels 906 is set off from the first range of pixels 904 vertically by the distance. As such, the second range of pixels 906 is oriented in a separate row of the image 900 from the first range of pixels 904. Upon the placement of the second range of pixels 906 in the image 900, the computing device may analyze the gray scale values of the pixels in the second range of pixels to determine the pixel or group of pixels with the lowest gray scale value. The edge of the cortical bone in the second range of pixels 906 may then be associated with the pixel with the lowest gray scale value. A third range of pixels 908 may then be created and placed in the image the distance d from the second range of pixels 906. The pixels of the third range of pixels 908 may be analyzed to determine the lowest gray scale value and the cortical bone edge within the third range of pixels.

In this manner, multiple ranges of pixels 904-916 may be created and analyzed to detect the edge of the cortical bone in the image 900. Further, the ranges of pixels 904-916 may be offset from each other by the distance d in any direction. For example, ranges of pixels 906-910 are oriented in rows above the reference point 902, while ranges of pixels 912-916 are oriented in ranges in rows below the reference point, with the distance between each range of pixels being the value d. Also, the placement of the ranges of pixels 904-916 may be in any direction from the reference pixel 902. Thus, ranges of pixels 904-916 may be horizontal or vertical from the first range of pixels 904. In addition, the ranges of pixels 904-916 may be in any orientation, such as vertical, horizontal, blocks, diagonal, etc. and may include more or fewer pixels than the first range of pixels 904. Finally, the distance between the ranges of pixels 904-916 may be any distance and may vary between the various ranges of pixels in the image 900. In this manner, the computing device may utilize pixel ranges 904-916 to locate the edge of the cortical bone in many locations within the image 900.

In one particular embodiment, the placement of the ranges of the pixels 904-916 may be adjusted upon the detection of the cortical bone edge in previous ranges of pixels. For example, upon the analysis of the second range of pixels 906 and the third range of pixels 908 in the image 900, the computing device may determine that the cortical bone is moving to the right within the ranges of pixels as the ranges of pixels are placed closer to the top of the image. In such a scenario, the computing device may begin orienting additional ranges of pixels to the right from the previous range of pixels. In this manner, the placement of the ranges of pixels may be adjusted as the cortical bone edge is determined through the analysis of previous ranges of pixels. In a similar manner, the orientation of the ranges of pixels may also be adjusted as the edge of the cortical bone is determined. In general, any configurable aspect of the range of pixels may be adjusted during the method described as more information about the location of the cortical bone edge is determined within the image.

Through the operations described above, a computing device may automatically determine or approximate the cortical bone or edge of the femur of a 2D image of a patient's hip joint. The location of the bone edge may aid a user of the computing device or the computing device itself in determining the anatomy of the patient's hip for use in a THA procedure. For example, from the 2D images of the patient's hip and, in particular, one or more landmarks of the patient's hip identified in the 2D images, an orientation of an implant in the acetabulum cavity of the patient may be determined for use during a hip replacement procedure. The one or more landmarks may coincide with one or more edges of the patient's bone in the images. In another example, a scraper or other device used during the THA procedure may be determined and/or oriented relative to the landmarks and anatomy calculated through the images. Thus, determining one or more edges of the patient's bone in the 2D images through the method described above may provide the one or more landmarks within the images to determine portions of the patient's anatomy used during the resection portion of the THA. Because the method described above is more accurate and/or quicker than the user manually identifying the edge of the bone edge in the images through a computing device interface, the use of the method may provide a more accurate implant or scrapping device for use during the hip replacement procedure.

One example of the use of the edge detection of the patient's bone in one or more 2D images of the patient's joint is now described. In particular, a cavity scraper device or jig that aligns with a femur neck central axis line may be created from the location of landmarks or other portions of the patient's anatomy. Such landmarks may be identified in one or more image slices of the patient's hip joint and applied to the cavity scraper device orientation. In one particular embodiment, one or more orientations or angles of the patient's anatomy may be utilized to create a customized scrapping jig for use during the THA procedure. In general, during a THA procedure, portions of the proximal end of the femur and acetabulum (such as that shown in FIG. 2) are removed by the surgeon and replaced with an implant that approximates the shape and function of the ends of the respective bones. To aid in resecting and/or aligning portions of the joint bones, the surgeon may employ a acetabulum cavity scrapping device that provides a clean or generally rounded surface in the cavity that mates with the femur end.

To determine the patient's anatomy, the computing device may receive the 2D images or image slices of the joint from an imaging device and create a customized scrapping jig template from the images. Once the template for the scrapping jig is created by the computing device utilizing one or more of the landmarks on the 2D images, a cutting or milling program is generated by the computing device. The cutting or milling program may then be provided to a milling machine to create the scrapping jig corresponding to the milling program. The scrapping jig is thus customized to the landmarks identified in the series of 2D images of the patient's joint. Further, the procedure does not require the generation of a three-dimensional (3D) model of the patient's anatomy to create the customized nature of the cutting jig. Rather, by utilizing one or more mating shapes that contact the joint anatomy at particular contact points of the joint anatomy corresponding to the identified landmarks in the 2D images, the customization of the scrapping jig is achieved. Further, because the procedure does not require the generation of a 3D model, the customized scrapping jigs may be produced more quickly and efficiently than previous customization methods.

Figure 10:
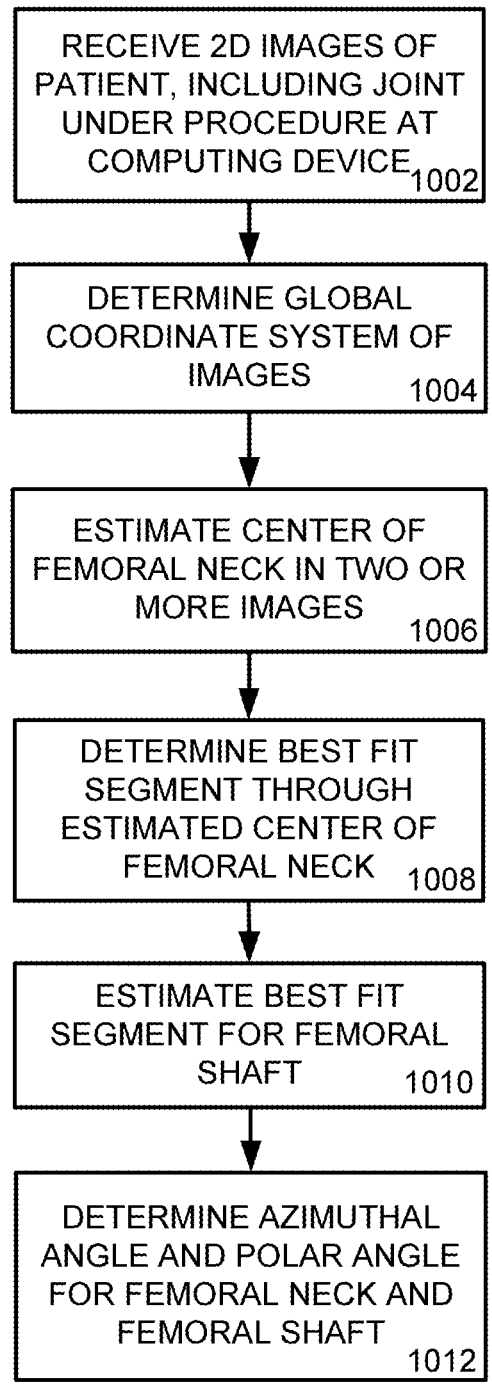
FIG. 10 is a flowchart illustrating a method for determining one or more lengths and/or angles of a patient's femur anatomy for use during a hip replacement procedure from one or more 2D images of the hip.

FIG. 10 is a flowchart illustrating a method for determining one or more lengths and/or angles of a patient's femur anatomy for use during a hip replacement procedure from one or more 2D images of the hip. The operations of the method of FIG. 10 may be performed by a computing device in operation by a user of the computing device. In addition, one or more of the operations may be performed by the computing device utilizing the cortical bone edge detection method discussed above. In general, the method provides one or more reference locations, lengths, and/or angles of the patient's anatomy for use in creating an implant or scrapping jig used during a THA procedure.

Beginning in operation 1002, a series of two-dimensional (2D) images of the patient's joint on which the arthroplasty procedure is to be performed may be obtained. The 2D images of the patient's joint may be obtained from an imaging device (such as an X-ray or magnetic resonance imaging (MRI) machine) from several aspects of the joint. Once the 2D images of the joint at issue are obtained, the images may be entered into a computing device for processing. The computing device may receive the images through any form of electronic communication with the imaging device. In one particular example, the 2D images may be obtained by the imaging device (such as the MRI imaging machine) and transmitted to a website accessible by the computing device. In general, however, the 2D images may be obtained from the imaging machine in any fashion for further processing by the computing device.

Figure 11:
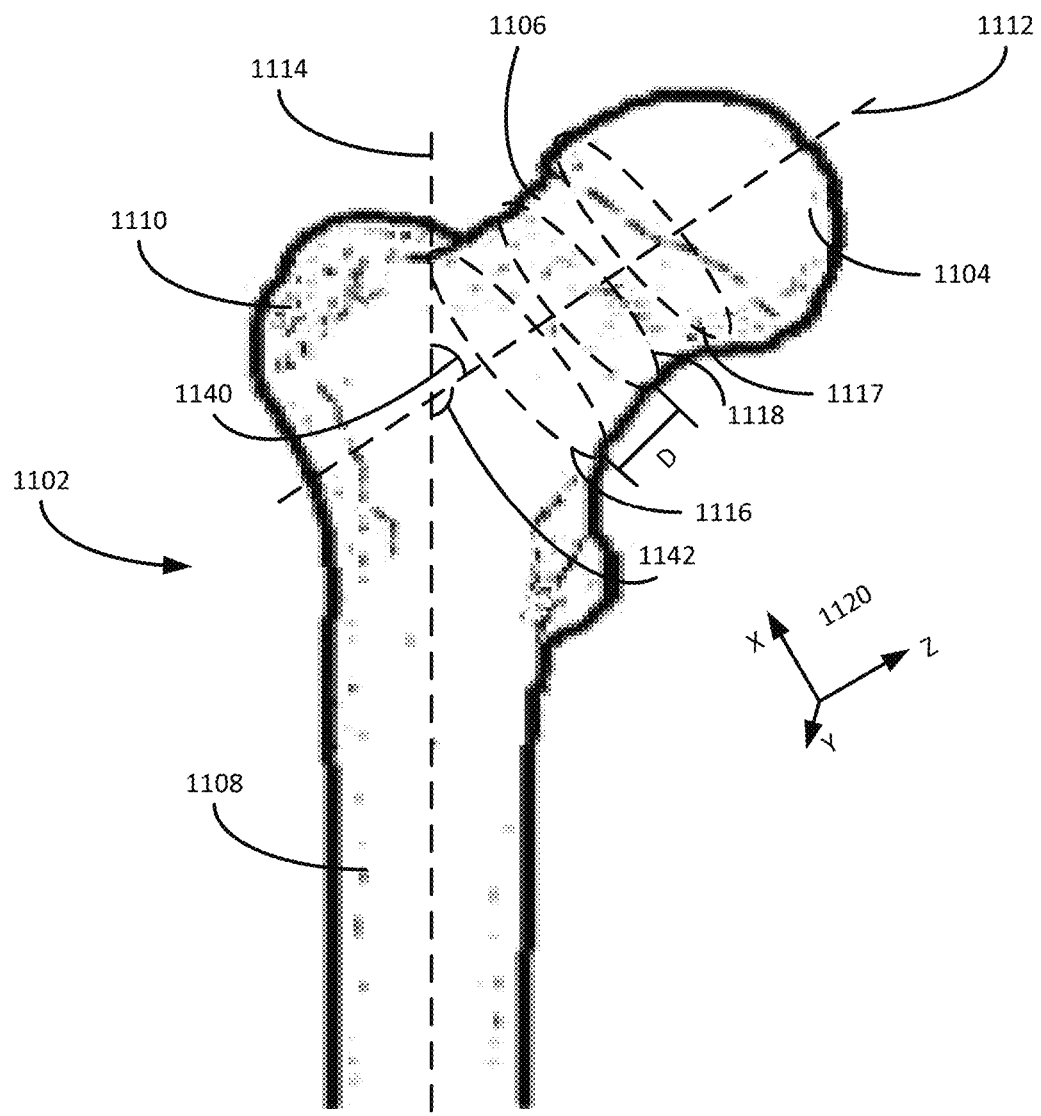
FIG. 11 is a perspective illustration of an upper (or proximal) portion of a femur of a patient.

In operation 1004, the 2D images of the joint are processed to determine a global coordinate system for the images and/or to identify one or more points or landmarks associated with the patient's joint. In general, a global coordinate system of the patient's joint in the images corresponds to the natural alignment of the patient prior to damage to the joint. One particular example of the global coordinate system is illustrated in FIG. 11. FIG. 11 is perspective illustration of an upper (or proximal) portion of a femur of a patient. Portions of the femur 1102 model may be illustrated in the one or more image slices of the patient's femur mentioned above. That is, the femur 1102 may be a collection of the image slices of the patient's femur such that portions of the femur of FIG. 11 correspond to portions of the patient's femur, as provided in the received 2D images. In particular and as discussed above, femur 1102 includes a femoral shaft 1108 and a femur head 1104. Extending laterally from the generally spherical femoral head 1104 is a cylindrically-shaped neck of the femur 1106, ending at a large, irregular, quadrilateral eminence of the femur known as the greater trochanter 1110. Also illustrated in the Figure are an estimated line through the center of the femur neck 1112 and an estimated line through the center of the femur shaft 1114. As discussed in more detail below, the femoral neck center axis (FNCA) 1112 and femoral shaft center axis (FSCA) 1114 may be determined by the computing device through an analysis of the images of the patient's femur 1102.

Also included in FIG. 11 is a global coordinate axis 1120. In general, the global coordinate system 1120 includes an x-axis, y-axis, and a z-axis. In one particular embodiment, the z-axis coincides with, or is approximately parallel to, a direction of a line segment through the femoral neck 1106, or the femoral neck center axis 1112. As such, the computing device may determine the FNCA 1112 directly from the images, or an approximation of the FNCA may be provided to the computing device, such as from a user of the device. In one specific example, the user may provide a center axis reference line in one or more of the images that approximates the FNCA 1112. Also, the x-axis and the y-axis of the global coordinate system 1120 may be oriented in a plane that is transverse or perpendicular to the z-axis. As should be appreciated, the global coordinate system 1120 of FIG. 11 is but one system that may be used in the present disclosure. In general, the global coordinate system 1120 may lie in any orientation in relation to the 2D images.

In one particular embodiment, one or more of the 2D images may be reformatted along the global coordinate system 1120. For example, the reformatting of the images may include reorientation of the images and/or extrapolation of data from between image slices to align or approximate the global coordinate system 1120. Thus, each of the 2D images in the set of images may be reformatted to account for the angle of the images obtained during imaging. In one embodiment, one or more reference lines or points within the images may be analyzed when reorienting or reformatting the images along the global coordinate system. Such reference points or reference lines may be obtained through the operations described above to locate the edge of the femur bone in the images provided to the computing device. In yet another embodiment, the global coordinate system 1120 may be determined by the computing device in relation to the image or images with no additional formatting of the images occurring.

In operation 1006, a computing device estimates the center coordinates of the femur neck 1106 in two or more of the 2D images that include the patient's femur 1102. In one particular embodiment, the computing device may utilize a sequence of approximately parallel images, spaced apart along the FNCA 1112 of the femur neck (along the z-axis of the global coordinate system 1120). As should be appreciated, however, it is not required that the images be along the z-axis, but may be oriented in any manner in the coordinate system 1120. Also, as described below, the computing device may utilize two or more such images when determining the center of the femur neck 1106 depicted in the images of the patient's femur 1102.

Viewed along the z-axis, the selected images form a general oval-shape, representing a cross-section view of the femur neck 1106. For example, FIG. 11 includes two such image slices through the femur neck 1106, cross-section image 1116 and cross-section image 1118. As shown, cross-section image 1116 and cross-section image 1118 are separated along the femur neck 1106 (and subsequently along the z-axis of the coordinate system 1120) by a distance d. In general, distance d between the images may be any distance along the femur neck 1106.

Figure 12:
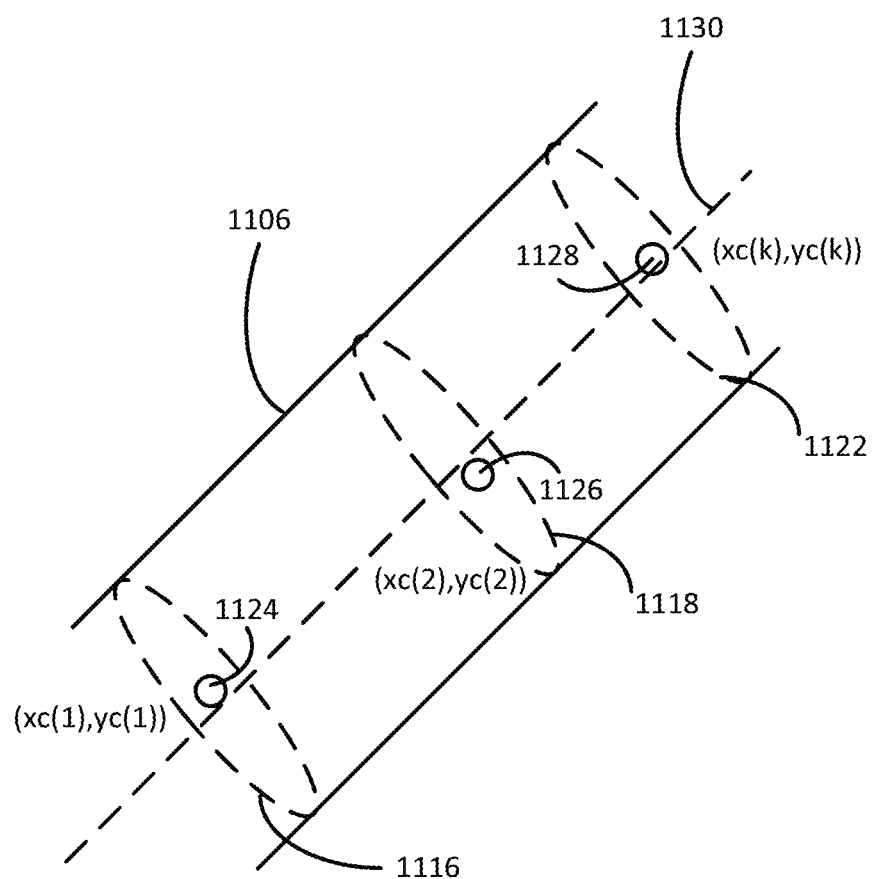
FIG. 12 is a perspective illustration of a femur neck, providing a best fit line that passes through or near the center axis of the femur neck.

Once the cross-section images 1116, 1118 are selected, the computing device may then estimate a center of the ovals in the selected images. For example, FIG. 12 is a perspective illustration of the femur neck 1106 of FIG. 11, including image slice 1116 and image slice 1118 through the neck. As mentioned, each slice through the femur neck 1106 provides a mostly oval-shape when viewed along the z-axis of the global coordinate system 1120. Thus, the computing device may estimate a center of the oval-shape for each of the image slices 1116, 1118 selected by the computing device. In particular, image slice 1116 includes estimated center point 1124 and image slice 1118 includes estimated center point 1126. Further, the computing device may determine a coordinate in the coordinate system associated with each estimated center point, such that center point 1124 may correspond to coordinate point $(x_c(1), y_c(1))$ and center point 1126 may correspond to coordinate point $(x_c(2), y_c(2))$. Further, additional images slices 1122 and center points 1128 (with associated coordinate points $((x_c(k), y_c(k))$ may be determined by the computing device. In general, any number of images slices may be selected by the computing device.

In one particular embodiment, a sequence of two dimensional coordinates $(xm(k), ym(k))$ (numbered m=1, . . . , M) of spaced apart locations on each oval (numbered k=1, . . . , K) is measured, and coordinates $(x_c(k), y_c(k))$ of geometric center for each oval are estimated as $$M(x_c(k), y_c(k)) = \Sigma(x_m(k), y_m(k))/M.$$

m=1

These points may then be assumed as the estimated centers of the selected image slices along the femur neck 1106 by the computing device.

Once the centers of the image slices 1116, 1118 through the femur neck 1106 are estimated, the computing device may determine a best fit linear segment adjacent to or near the estimated image slice centers in operation 1008. One best fit linear segment 1130 is shown in FIG. 12 for the image slices 1116, 1118 through the femur neck 1106. In general, the best fit linear segment 1130 may be determined by the computing device by minimizing an error function that provides a measure of an error between each of the center coordinate locations and the coordinates of the best fit linear segment as the segment passes through the associated image slice. In this manner, the best fit linear segment 1130 is created that passes through or near the center coordinates 1124-1128 of the image slices along the femur neck 1106. In one embodiment, the best fit linear segment 1130 may be utilized by the computing device as a femur neck central axis (FNCA) line 1112 through the femur neck 1106. As described in more detail below, a cut plane used during a hip replacement procedure may be determined by the computing device as being perpendicular to the FNCA 1112 line through the femur neck 1106.

In a similar manner in determining the FNCA line 1112 through the neck 1106 of the femur, the computing device may determine a best fit linear segment for the femur shaft 1108 in operation 1010. Thus, in one embodiment, the computing device may obtain image slices through the femur shaft 1108, estimate a center of two or more images through the femur shaft, and calculate a best fit segment line 1114 through or near the determined center coordinates of the selected image slices. This line through the femur shaft 1108 may be utilized by the computing device as the femur shaft central axis (FSCA) line 1114.

In operation 1012, the computing device may then calculate an azimuthal angle φ 1140 and a polar angle θ 1142 of the FNCA 1112 relative to the FSCA 1114. In particular, the two angles (the azimuthal angle φ and a polar angle θ) may be estimated or calculated by the computing device utilizing two or three transversely oriented views of the femur neck 1106 and the femur shaft 1108 relative to each other. In other words, by knowing the orientation of the FSCA 1114 and the FNCA 1112 in the global coordinate system 1120, the computing device calculates the azimuthal angle φ 1140 and a polar angle θ 1142 between the two line segments. The azimuthal angle φ 1140 and a polar angle θ 1142 are illustrated in FIG. 11, although it should be appreciated that these angles lie in the three-dimensional global coordinate system 1120 of the Figure.

Figure 13:
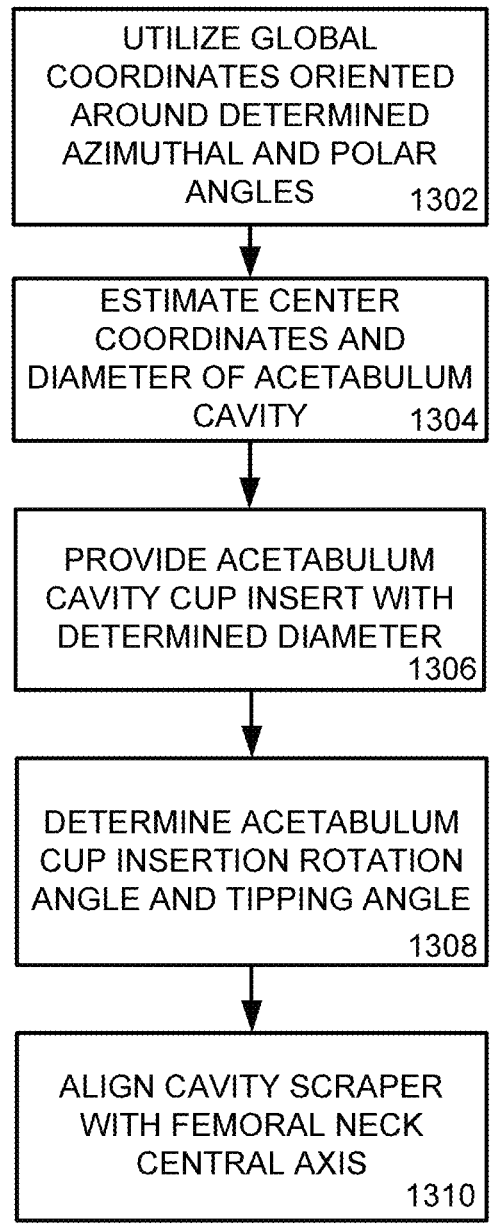
FIG. 13 is a flowchart of a method for determining an alignment for an acetabulum implant and/or jig mechanism for use during a hip replacement procedure.

As explained above, the axes and angles determined from the images of the patient's anatomy may be utilized to determine the placement of an acetabulum cavity implant and/or a jig mechanism for use in scrapping the surface of the acetabulum cavity. In particular, FIG. 13 is a flowchart of a method for determining an alignment for an acetabulum implant and/or jig mechanism for use during a hip replacement procedure. Similar to above, the operations of the method of FIG. 13 may be performed by a computing device in operation by a user of the computing device. In addition, one or more of the operations may be performed by the computing device utilizing the cortical bone edge detection method discussed above.

Beginning in operation 1302, the computing device may utilize the global coordinates determined above. In particular, the global coordinate system 1120 may include an x-axis, y-axis, and a z-axis. In one particular embodiment, the z-axis coincides with, or is approximately parallel to, a direction of a line segment through the femoral neck 1106, or the femoral neck center axis 1112, as shown in FIG. 11. As also described above, the computing device may calculate the azimuthal angle φ 1140 and a polar angle θ 1142 of the FNCA 1112 relative to the FSCA 1114. In other words, by knowing the orientation of the FSCA 1114 and the FNCA 1112 in the global coordinate system 1120, the computing device calculates the azimuthal angle φ 1140 and a polar angle θ 1142 between the two line segments. Thus, the z-axis of the global coordinate system 1120 is oriented at the azimuthal angle φ 1140 and a polar angle θ 1142 relative to the FSCA 1114. In one particular embodiment, the z-axis may also coincide with an initial central axis for an acetabulum cavity cup insert that may be used during a hip replacement procedure, discussed in more detail below.

In operation 1304, the computing device may estimate center location coordinates in the global coordinate system and a radius or diameter length for the patient's acetabulum cavity. In one embodiment, the computing device analyzes one or more images of the patient's anatomy and, utilizing four or more non-coplanar locations on an exposed surface of the acetabulum cavity, estimates the center location coordinates and/or the radius of the cavity. In another embodiment, the computing device may receive one or more electronic markers within one or more of the patient images that indicate the center location and/or radius of the acetabulum cavity, or provides landmarks within the images from which the center coordinates and/or radius may be calculated.

With the radius of the acetabulum cavity estimated, an appropriately sized insert or implant used in the THR procedure may be selected or determined. In particular, the insert may be twice the estimated radius or the estimated diameter determined above. In general, acetabulum cavity implants may come in various sizes such that an appropriately sized implant similar to the patient's anatomy may be selected for use during the THR procedure.

Although an appropriately sized acetabulum cavity implant is determined, the orientation of the implant in the patient's acetabulum cavity may still be determined by the computing device. In particular, a concern of hip replacement devices is the possibility that an implant oriented on the femur head or the femur head itself, when installed in an acetabulum cavity, will become subsequently dislocated from the cavity. In order to minimize this possibility, in one alternative the acetabulum cup insert, which normally covers a solid angle ΔSA of about $2\pi$ steradians (e.g., a hemisphere) is optionally provided with a solid angle ΔSA' that is about 1-6 percent greater than the normal value of $2\pi$ steradians. This provides an acetabulum cavity that has a hyper-hemisphere shape (covering slightly greater than a hemisphere), having a corresponding solid angle, covering slightly more than $2\pi$ steradians. In other words, proper orientation of the acetabulum cavity implant may reduce the occurrence of dislocation of the femur from the acetabulum cavity implant, post-procedure.

Orientation of the acetabulum cavity implant in the acetabulum cavity may be determined by the computing device with reference to a determined insertion rotation angle and tipping angle, in operation 1308. In particular, the central axis of the acetabulum cavity implant may be rotated within the acetabulum cavity, relative to the initial acetabulum cavity central axis determined above, by a selected implant insert rotation angle $\psi s$ and by a selected tipping angle $\eta s$, where $\psi s$ lies in a range $-20° \leq \psi s \geq -40°$ and $\eta s$ lies in a range $0° \leq \eta s \geq 15°$. Generally, the angles are chosen to ensure that the hip implant or reshaped femur head rotates within the acetabulum cavity insert but is unlikely to dislocate from the acetabulum cavity insert in normal use. In one embodiment, the angles $\psi s$ and $\eta s$ are selected or determined by the surgeon prior to the procedure to resist dislocation of the acetabulum cavity insert, the implant femur head and/or the implant femur neck from the resulting (scraped) acetabulum cavity.

The resulting angular orientation of the acetabulum cavity insert central axis, relative to the femur shaft central axis FSCA, can be expressed as a rotation matrix:

$$R = R2(\eta s) R3(\psi s) R2(\theta) R3(\varphi).$$

The four rotations indicated in the equation may be collectively characterized as a four-stage Eulerian angle transformation and may be expressed as ordered rotations by the angles $\varphi$, $\theta$, $\psi s$, and $\eta s$.

Generally, where the acetabulum cavity insert tipping angle $\eta s$ is chosen to be 0, all rotations by the angle $\psi s$ will merely rotate the acetabulum cavity insert about the original femur neck central axis and, practically, will result in the same cumulative rotation R, which is now determined only by the angle pair ($\varphi$, $\theta$) that characterizes the angular orientation of the femur neck central axis relative to the femur shaft central axis. Where the final tipping angle $\eta s$ is non-zero, the total rotation R is preferably chosen to provide a constraint for the (rotated) acetabulum cavity insert that resists dislocation of the acetabulum cavity insert and implant femur head and/or implant femur neck from the acetabulum cavity.

Figure 14:
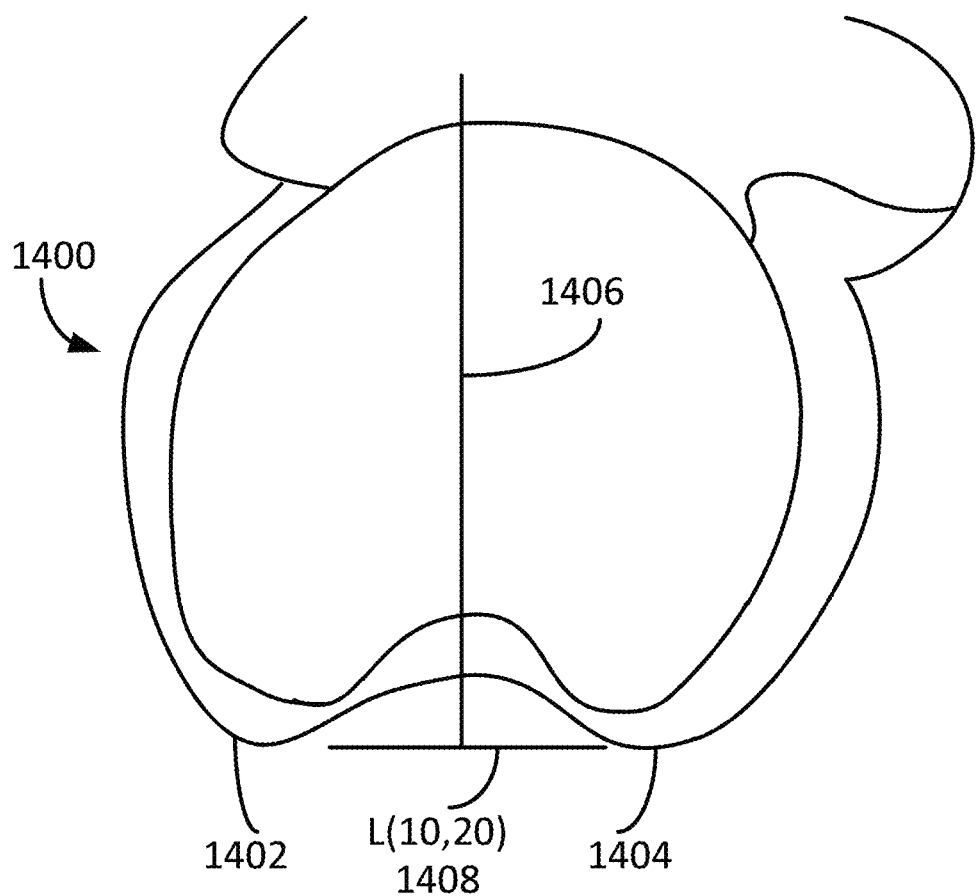
FIG. 14 is a perspective illustration of an acetabulum cavity of a patient, illustrating a first portal location and a second portal location associated with the acetabulum cavity.

In one particular embodiment, landmarks associated with the acetabulum cavity obtained from the plurality of images of the patient's anatomy may be utilized to determine the insertion rotation $\psi s$ of the acetabulum cavity insert. In particular, FIG. 14 illustrates a first portal location 1402 and a second portal location 1404 associated with the acetabulum cavity 1400, viewed in a direction approximately parallel to the femur neck central axis. The portal locations, 1402, 1404 are located at first and second edge points of a dip or declension in a perimeter of the acetabulum cavity. The view shown in FIG. 14 is generally oriented parallel to the femur neck central axis.

To determine an insertion rotation $\psi s$ of the acetabulum cavity insert, coordinates for the first portal location (referred to herein as (x10,y10,z10)) and coordinates for the second portal location (referred to herein as (x20,y20,z20)) for the cavity that faces the femur neck are estimated by the computing device. These coordinates are referenced to the global coordinate system discussed above. The portal locations, 1402, 1404, are associated with a small dip or opening in the acetabulum cavity that faces one end of the femur neck and femur head as shown in the patient images. Coordinates describing a perpendicular bisector plane 1406 of a line segment L(10,20) 1408 that extends between the first and second portal locations 1402, 1404 are estimated. The bisector plane 1406 intersects a perimeter of the cavity at a point that also defines a location on the acetabulum cavity insert from which the angles $\psi s$ and $\eta s$ are measured. In this embodiment, the acetabulum cavity insert rotation angle $\psi s$ is determined by a normal vector n(10,20) that is parallel to the line segment L(1020) 1408 illustrated in FIG. 14. In this manner, the insertion rotation angle $\psi s$ may be determined from the images of the patient as a normal vector n(10,20) from the line segment L(10,20) 1408 that extends between the first and second portal locations, 1402, 1404.

In operation 1310, a jig mechanism may be created and/or provided based on one or more of the calculations made above that aligns a cavity scraper with the femur neck central axis. The cavity scraper may remove at least one bony projection form an exposed surface of the acetabulum cavity. The alignment of the jig mechanism may be in relation to the insert orientation performed above such that the scraping of the acetabulum cavity provides a mating surface for the acetabulum cavity insert.

Figure 15:
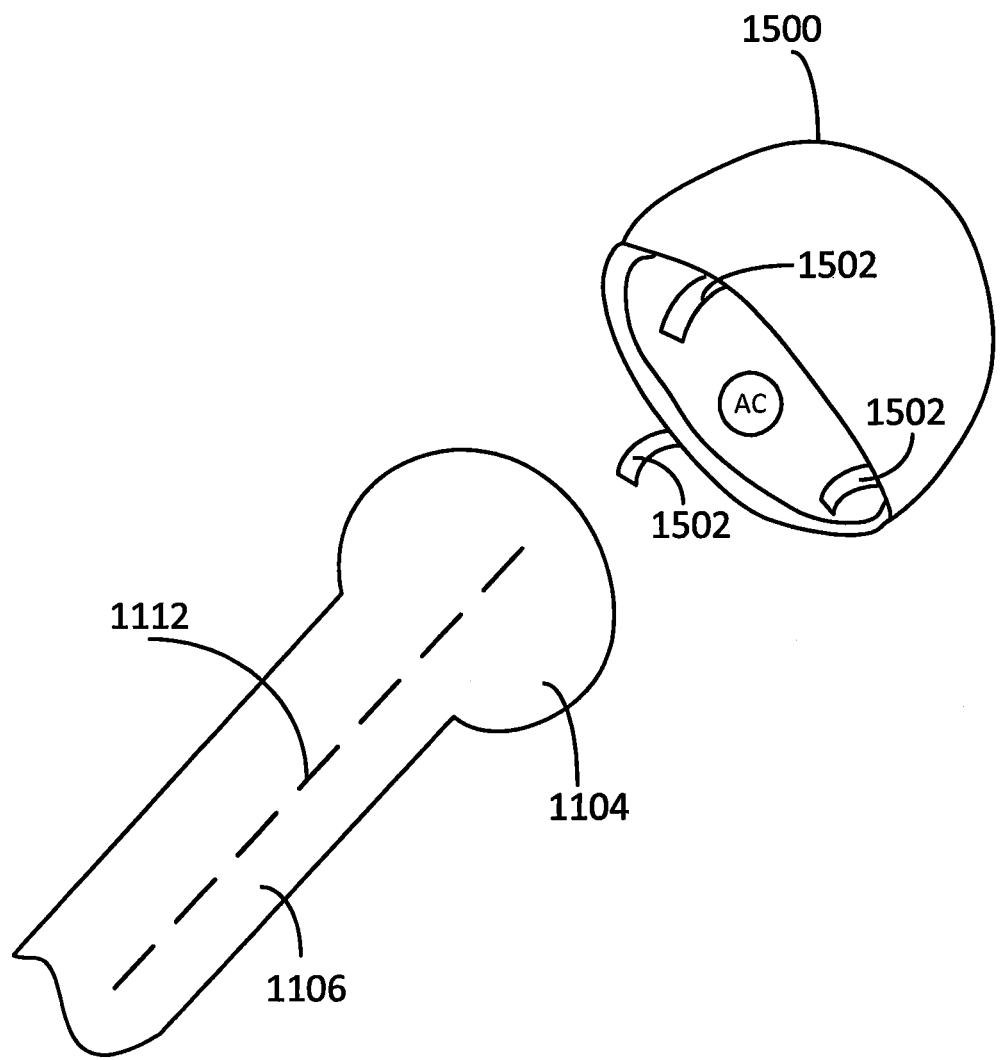
FIG. 15 is perspective view of a jig mechanism for use with one or more embodiments of the present disclosure.

In a first embodiment of the acetabulum cavity insert, a plurality of detents or projections may be utilized on a perimeter of the acetabulum cavity insert to provide a mechanism for grasping or holding an implant femur head within the cavity implant. FIG. 15 illustrates an alternative embodiment for resisting dislocation of a femur head implant. In particular, a perimeter of the acetabulum cavity insert 1500 is provided with three or more spaced apart projections or detents 1502 are positioned and oriented so that, when the acetabulum cavity insert receives an implant femur head, the projections grasp and hold the implant femur head and resist separation of the implant femur head from the acetabulum cavity insert. The implant femur head can be removed or dislocated from the acetabulum cavity insert only with application of substantial force; and in ordinary use, the implant femur head and the acetabulum cavity insert remain together.

Figure 16:
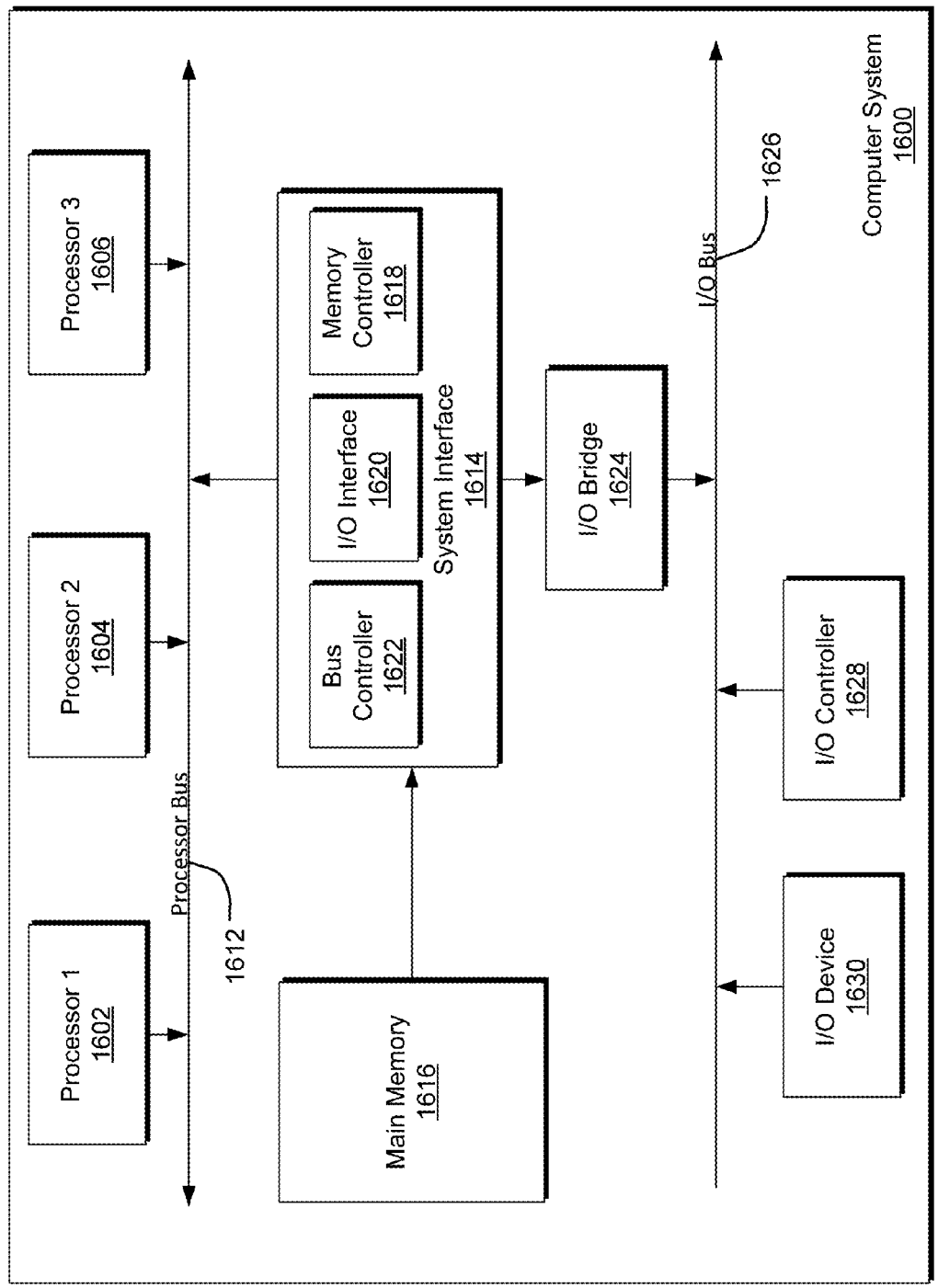
FIG. 16 is a block diagram illustrating an example of a computing device or computer system which may be used in implementing the embodiments disclosed above.

FIG. 16 is a block diagram illustrating an example of a computing device or computer system 1600 which may be used in implementing the embodiments disclosed above. The computer system (system) includes one or more processors 1602-1606. Processors 1602-1606 may include one or more internal levels of cache (not shown) and a bus controller or bus interface unit to direct interaction with the processor bus 1612. Processor bus 1612, also known as the host bus or the front side bus, may be used to couple the processors 1602-1606 with the system interface 1614. System interface 1614 may be connected to the processor bus 1612 to interface other components of the system 1600 with the processor bus 1612. For example, system interface 1614 may include a memory controller 1618 for interfacing a main memory 1616 with the processor bus 1612. The main memory 1616 typically includes one or more memory cards and a control circuit (not shown). System interface 1614 may also include an input/output (I/O) interface 1620 to interface one or more I/O bridges or I/O devices with the processor bus 1612. One or more I/O controllers and/or I/O devices may be connected with the I/O bus 1626, such as I/O controller 1628 and I/O device 1630, as illustrated.

I/O device 1630 may also include an input device (not shown), such as an alphanumeric input device, including alphanumeric and other keys for communicating information and/or command selections to the processors 1602-1606. Another type of user input device includes cursor control, such as a mouse, a trackball, or cursor direction keys for communicating direction information and command selections to the processors 1602-1606 and for controlling cursor movement on the display device.

System 1600 may include a dynamic storage device, referred to as main memory 1616, or a random access memory (RAM) or other computer-readable devices coupled to the processor bus 1612 for storing information and instructions to be executed by the processors 1602-1606. Main memory 1616 also may be used for storing temporary variables or other intermediate information during execution of instructions by the processors 1602-1606. System 1600 may include a read only memory (ROM) and/or other static storage device coupled to the processor bus 1612 for storing static information and instructions for the processors 1602-1606. The system set forth in FIG. 16 is but one possible example of a computer system that may employ or be configured in accordance with aspects of the present disclosure.

According to one embodiment, the above techniques may be performed by computer system 1600 in response to processor 1604 executing one or more sequences of one or more instructions contained in main memory 1616. These instructions may be read into main memory 1616 from another machine-readable medium, such as a storage device. Execution of the sequences of instructions contained in main memory 1616 may cause processors 1602-1606 to perform the process steps described herein. In alternative embodiments, circuitry may be used in place of or in combination with the software instructions. Thus, embodiments of the present disclosure may include both hardware and software components.

A machine readable medium includes any mechanism for storing or transmitting information in a form (e.g., software, processing application) readable by a machine (e.g., a computer). Such media may take the form of, but is not limited to, non-volatile media and volatile media. Non-volatile media includes optical or magnetic disks. Volatile media includes dynamic memory, such as main memory 1616. Common forms of machine-readable medium may include, but is not limited to, magnetic storage medium; optical storage medium (e.g., CD-ROM); magneto-optical storage medium; read only memory (ROM); random access memory (RAM); erasable programmable memory (e.g., EPROM and EEPROM); flash memory; or other types of medium suitable for storing electronic instructions.

It should be noted that the flowcharts above are illustrative only. Alternative embodiments of the present invention may add operations, omit operations, or change the order of operations without affecting the spirit and scope of the present invention. The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

The invention claimed is:

1. A method for determining an orientation of an implant for an arthroplasty procedure on a human hip joint, the method comprising:

receiving a plurality of two-dimensional (2D) images of a patient's joint subject to the arthroplasty procedure at a computing device;

providing a sequence of interior images of a neck of a femur from the plurality of 2D images of the patient's joint, the interior images corresponding to cross-section images of the neck of the femur and spaced apart by a positive distance;

estimating a center coordinate for each of the sequence of interior images of the neck of the femur, the center coordinate corresponding to a coordinate in a global coordinate system of the plurality of 2D images of the patient's joint;

calculating a best fit linear segment corresponding to at least two of the center coordinates for the sequence of interior images of the neck of the femur;

estimating a center coordinate and a diameter for an acetabulum feature of the patient from at least one of the plurality of 2D images of the patient's joint;

providing an acetabulum cavity cup insert comprising a diameter corresponding to the estimated diameter for the acetabulum feature of the patient from at least one of the plurality of 2D images of the patient's joint; and aligning the center of the acetabulum cavity cup insert with the best fit linear segment corresponding to at least two of the center coordinates for the sequence of interior images of the neck of the femur;

wherein said best fit linear segment is determined by said computing device by minimizing an error function that provides a measure of an error between each of the center coordinate locations and the coordinates of said best fit linear segment as said femur.

2. The method of claim 1 wherein the global coordinate system of the plurality of 2D images of the patient's joint comprises a z-axis oriented approximately parallel to a longitudinal axis of the femur neck and an xy-plane oriented perpendicular to the z-axis and wherein the sequence of interior images of the neck of the femur is oriented perpendicular to the z-axis.

3. The method of claim 1 further comprising:
estimating a best fit linear segment for a shaft of the femur; and
calculating an azimuthal angle and a polar angle for the orientation of a direction of the best fit linear segment corresponding to at least two of the center coordinates for the sequence of interior images of the neck of the femur relative to a direction of the best fit linear segment for a shaft of the femur.

4. The method of claim 1 further comprising:
providing a jig mechanism configured to align a cavity scraper in the patient's acetabulum cavity, the cavity scraper configured to remove at least one bony projection from an exposed surface of the acetabulum cavity.

5. The method of claim 4 further comprising:
aligning a center of the cavity scraper with the best fit linear segment corresponding to at least two of the center coordinates for the sequence of interior images of the neck of the femur.

6. The method of claim 3 further comprising:
calculating an acetabulum cavity cup insert rotation angle relative to at least the calculated azimuthal angle and the polar angle, the acetabulum cavity cup insert rotation angle indicating an angle of rotation of the acetabulum cavity cup insert in the patient's acetabulum cavity.

7. The method of claim 3 further comprising:
calculating an acetabulum cavity cup insert tipping angle relative to at least the calculated azimuthal angle and the polar angle, the acetabulum cavity cup insert tipping angle indicating an orientation angle of the acetabulum cavity cup insert in the patient's acetabulum cavity.

8. A system for processing a medical scan of a patient in preparation for an arthroplasty procedure on a human hip joint, the system comprising:
a network interface configured to receive one or more medical images of a patient's anatomy;
a processing device in communication with the network interface;
a computer-readable medium in communication with the processing device configured to store information and instructions that, when executed by the processing device, performs the operations of:
receiving a plurality of two-dimensional (2D) images of a patient's joint subject to the arthroplasty procedure at a computing device;
providing a sequence of interior images of a neck of a femur from the plurality of 2D images of the patient's joint, the interior images corresponding to cross-section images of the neck of the femur and spaced apart by a positive distance;
estimating a center coordinate for each of the sequence of interior images of the neck of the femur, the center coordinate corresponding to a coordinate in a global coordinate system of the plurality of 2D images of the patient's joint;
calculating a best fit linear segment corresponding to at least two of the center coordinates for the sequence of interior images of the neck of the femur;
estimating a center coordinate and a diameter for an acetabulum feature of the patient from at least one of the plurality of 2D images of the patient's joint; and
an acetabulum cavity cup insert comprising a diameter corresponding to the estimated diameter for the acetabulum feature of the patient from at least one of the plurality of 2D images of the patient's joint, a center of the acetabulum cavity cup insert aligned with the best fit linear segment corresponding to at least two of the center coordinates for the sequence of interior images of the neck of the femur;
wherein said best fit linear segment is determined by said computing device by minimizing an error function that provides a measure of an error between each of the center coordinate locations and the coordinates of said best fit linear segment as said best fit linear segment passes through a plurality of image slices along said neck of said femur.

9. The system of claim 8 wherein the global coordinate system of the plurality of 2D images of the patient's joint comprises a z-axis oriented approximately parallel to a longitudinal axis of the femur neck and an xy-plane oriented perpendicular to the z-axis and wherein the sequence of interior images of a neck of a femur is oriented perpendicular to the z-axis.

10. The system of claim 8 wherein the instructions, when executed by the processing device, further performs the operations of:
estimating a best fit linear segment for a shaft of the femur; and
calculating an azimuthal angle and a polar angle for the orientation of a direction of the best fit linear segment corresponding to at least two of the center coordinates for the sequence of interior images of the neck of the femur relative to a direction of the best fit linear segment for a shaft of the femur.

11. The system of claim 10 further comprising a jig mechanism configured to align a cavity scraper in the patient's acetabulum cavity, the cavity scraper configured to remove at least one bony projection from an exposed surface of the acetabulum cavity.

12. The system of claim 11 wherein a center of the cavity scraper aligns with the best fit linear segment corresponding to at least two of the center coordinates for the sequence of interior images of the neck of the femur.

13. The system of claim 10 wherein the instructions, when executed by the processing device, further performs the operations of: calculating an acetabulum cavity cup insert rotation angle relative to at least the calculated azimuthal angle and the polar angle, the acetabulum cavity cup insert rotation angle indicating an angle of rotation of the acetabulum cavity cup insert in the patient's acetabulum cavity.

14. The method of claim 10 wherein the instructions, when executed by the processing device, further performs the operations of:
calculating an acetabulum cavity cup insert tipping angle relative to at least the calculated azimuthal angle and the polar angle, the acetabulum cavity cup insert tipping angle indicating an orientation angle of the acetabulum cavity cup insert in the patient's acetabulum cavity.

15. A method for preparing an acetabulum cavity of a human hip joint, the method comprising: receiving a plurality of two-dimensional (2D) images of a patient's joint subject to the arthroplasty procedure at a computing device;
providing a sequence of interior images of a neck of a femur from the plurality of 2D images of the patient's joint, the interior images corresponding to cross-section images of the neck of the femur and spaced apart by a positive distance;
estimating a center coordinate for each of the sequence of interior images of the neck of the femur, the center coordinate corresponding to a coordinate in a global coordinate system of the plurality of 2D images of the patient's joint;
calculating a best fit linear segment corresponding to at least two of the center coordinates for the sequence of interior images of the neck of the femur;
estimating a center coordinate and a diameter for an acetabulum feature of the patient from at least one of the plurality of 2D images of the patient's joint; and
providing a jig mechanism configured to align a cavity scraper in the patient's acetabulum cavity, the cavity scraper configured to remove at least one bony projection from an exposed surface of the acetabulum cavity, the center of the cavity scraper aligned with the best fit linear segment corresponding to at least two of the center coordinates for the sequence of interior images of the neck of the femur;
wherein said best fit linear segment is determined by said computing device by minimizing an error function that provides a measure of an error between each of the center coordinate locations and the coordinates of said best fit linear segment as said femur.

16. The method of claim 15 wherein the global coordinate system of the plurality of 2D images of the patient's joint comprises a z-axis oriented approximately parallel to a longitudinal axis of the femur neck and an xy-plane oriented perpendicular to the z-axis and wherein the sequence of interior images of the neck of the femur is oriented perpendicular to the z-axis.

17. The method of claim 16 further comprising:
estimating a best fit linear segment for a shaft of the femur; and
calculating an azimuthal angle and a polar angle for the orientation of a direction of the best fit linear segment corresponding to at least two of the center coordinates for the sequence of interior images of the neck of the femur relative to a direction of the best fit linear segment for a shaft of the femur.

18. The method of claim 15 further comprising:
providing an acetabulum cavity cup insert comprising a diameter corresponding to the estimated diameter for the acetabulum feature of the patient from at least one of the plurality of 2D images of the patient's joint.

19. The method of claim 18 further comprising:
aligning the center of the acetabulum cavity cup insert with the best fit linear segment corresponding to at least two of the center coordinates for the sequence of interior images of the neck of the femur.

* * * * *